(12) United States Patent
Arnal et al.

(10) Patent No.: US 7,422,557 B2
(45) Date of Patent: Sep. 9, 2008

(54) NEEDLE DESIGN FOR MALE TRANSOBTURATOR SLING

(75) Inventors: Kevin R. Arnal, Excelsior, MN (US); Christian Gozzi, Via Fiumes (IT); Peter Rehder, Igls (AU)

(73) Assignee: AMS Research Corporation, Minnetonka, MN (US)

( * ) Notice: Subject to any disclaimer, the term of this patent is extended or adjusted under 35 U.S.C. 154(b) by 177 days.

(21) Appl. No.: 11/347,553

(22) Filed: Feb. 3, 2006

(65) Prior Publication Data

US 2006/0235262 A1 Oct. 19, 2006

Related U.S. Application Data

(60) Provisional application No. 60/683,185, filed on May 20, 2005, provisional application No. 60/677,457, filed on May 4, 2005, provisional application No. 60/659,504, filed on Mar. 8, 2005, provisional application No. 60/659,714, filed on Mar. 8, 2005, provisional application No. 60/650,207, filed on Feb. 4, 2005, provisional application No. 60/650,208, filed on Feb. 4, 2005, provisional application No. 60/650,209, filed on Feb. 4, 2005.

(51) Int. Cl.
*A61F 2/02* (2006.01)

(52) U.S. Cl. ............................................. 600/30

(58) Field of Classification Search ............. 600/29–31, 600/37; 606/119, 139, 151, 190; 128/885, 128/897, 898
See application file for complete search history.

(56) References Cited

U.S. PATENT DOCUMENTS

| | | | |
|---|---|---|---|
| 4,827,940 A | 5/1989 | Mayer et al. | |
| 5,112,344 A | 5/1992 | Petros | |
| 5,531,783 A | 7/1996 | Giele et al. | |
| 5,611,515 A | 3/1997 | Benderev et al. | |
| 5,716,391 A | 2/1998 | Grandjean | |
| 5,842,478 A | 12/1998 | Benderev et al. | |
| 5,860,425 A | 1/1999 | Benderev et al. | |
| 5,899,909 A | 5/1999 | Claren et al. | |
| 6,039,686 A | 3/2000 | Kovac | |
| 6,042,534 A | 3/2000 | Gellman et al. | |

(Continued)

FOREIGN PATENT DOCUMENTS

DE 20204669 9/2003

(Continued)

OTHER PUBLICATIONS

Rios, Luis, A.S., Male Perineal Sling with Autologous Aponeurosis and Bone Fixation—Description of a Technical Modification, Int'l Braz. J. Urol. vol. 29 (6), 524-527 (Nov.-Dec. 2003).

(Continued)

*Primary Examiner*—Charles A. Marmor, II
*Assistant Examiner*—Christine D Hopkins
(74) *Attorney, Agent, or Firm*—Jose' W. Jimenez; Kimberly K. Baxter; Gregory L. Koeller

(57) ABSTRACT

Described are surgical instruments for use in surgical procedures, related methods, systems, and kits, the instruments including features that optionally include one or more specific dimensions, and features that may result in an ergonomic advantage during use.

26 Claims, 16 Drawing Sheets

U.S. PATENT DOCUMENTS

| | | | |
|---|---|---|---|
| 6,042,536 | A | 3/2000 | Tihon et al. |
| 6,110,101 | A | 8/2000 | Tihon et al. |
| 6,273,852 | B1 | 8/2001 | Lehe et al. |
| 6,382,214 | B1 | 5/2002 | Raz et al. |
| 6,406,423 | B1 | 6/2002 | Scetbon |
| 6,475,139 | B1 | 11/2002 | Miller |
| 6,478,727 | B2 | 11/2002 | Scetbon |
| 6,575,897 | B1 | 6/2003 | Ory et al. |
| 6,582,443 | B2 | 6/2003 | Cabak et al. |
| 6,612,977 | B2 | 9/2003 | Staskin et al. |
| 6,638,210 | B2 | 10/2003 | Berger |
| 6,638,211 | B2 | 10/2003 | Suslian et al. |
| 6,641,524 | B2 | 11/2003 | Kovac |
| 6,641,525 | B2 | 11/2003 | Rocheleau et al. |
| 6,652,450 | B2 | 11/2003 | Neisz et al. |
| 6,689,047 | B2 | 2/2004 | Gellman |
| 6,691,711 | B2 | 2/2004 | Raz et al. |
| 6,702,827 | B1 | 3/2004 | Lund et al. |
| 6,755,781 | B2 | 6/2004 | Gellman |
| 6,802,807 | B2 | 10/2004 | Anderson et al. |
| 6,808,486 | B1 | 10/2004 | O'Donnell |
| 6,884,212 | B2 | 4/2005 | Thierfelder et al. |
| 6,908,425 | B2 | 6/2005 | Luscombe |
| 6,911,002 | B2 | 6/2005 | Fierro |
| 6,911,003 | B2 | 6/2005 | Anderson et al. |
| 6,953,428 | B2 | 10/2005 | Gellman et al. |
| 6,981,944 | B2 | 1/2006 | Jamiolkowski et al. |
| 6,991,597 | B2 | 1/2006 | Gellman et al. |
| 7,025,063 | B2 | 4/2006 | Snitkin et al. |
| 7,037,255 | B2 | 5/2006 | Inman et al. |
| 7,070,556 | B2 | 7/2006 | Anderson et al. |
| 7,070,558 | B2 | 7/2006 | Gellman et al. |
| 7,083,568 | B2 | 8/2006 | Neisz et al. |
| 2002/0147382 | A1 | 10/2002 | Neisz et al. |
| 2002/0151909 | A1 | 10/2002 | Gellman et al. |
| 2002/0156489 | A1 | 10/2002 | Gellman et al. |
| 2003/0009181 | A1 | 1/2003 | Gellman et al. |
| 2003/0130670 | A1 | 7/2003 | Anderson et al. |
| 2003/0199732 | A1 | 10/2003 | Suslian et al. |
| 2003/0212305 | A1* | 11/2003 | Anderson et al. ............ 600/29 |
| 2003/0220538 | A1 | 11/2003 | Jacquetin |
| 2004/0006353 | A1 | 1/2004 | Bosley, Jr. et al. |
| 2004/0087970 | A1 | 5/2004 | Chu et al. |
| 2004/0193215 | A1 | 9/2004 | Harari et al. |
| 2004/0230092 | A1 | 11/2004 | Thierfelder et al. |
| 2004/0231678 | A1 | 11/2004 | Fierro |
| 2004/0249240 | A1 | 12/2004 | Goldmann et al. |
| 2005/0004424 | A1 | 1/2005 | Raz et al. |
| 2005/0021086 | A1 | 1/2005 | De Leval |
| 2005/0027220 | A1 | 2/2005 | Wagner et al. |
| 2005/0038451 | A1 | 2/2005 | Rao et al. |
| 2005/0038452 | A1 | 2/2005 | Chu |
| 2005/0043580 | A1 | 2/2005 | Watschke et al. |
| 2005/0065395 | A1 | 3/2005 | Mellier |
| 2005/0075660 | A1 | 4/2005 | Chu et al. |
| 2005/0080317 | A1 | 4/2005 | Merade |
| 2005/0129733 | A1 | 6/2005 | Milbocker et al. |
| 2005/0131274 | A1 | 6/2005 | Suslian et al. |
| 2005/0143618 | A1 | 6/2005 | Anderson et al. |
| 2005/0245787 | A1 | 11/2005 | Cox et al. |
| 2005/0261545 | A1 | 11/2005 | Gellman et al. |
| 2005/0267325 | A1 | 12/2005 | Bouchier et al. |
| 2006/0009673 | A1 | 1/2006 | Chan |
| 2006/0195007 | A1 | 8/2006 | Anderson et al. |
| 2006/0195010 | A1 | 8/2006 | Arnal et al. |
| 2006/0195011 | A1 | 8/2006 | Arnal et al. |
| 2006/0247490 | A1 | 11/2006 | Merade et al. |
| 2006/0287571 | A1 | 12/2006 | Gozzi et al. |

FOREIGN PATENT DOCUMENTS

| | | |
|---|---|---|
| EP | 1342450 | 9/2003 |
| EP | 1248567 | 3/2004 |
| EP | 1151722 | 8/2004 |
| WO | WO 98/35632 | 8/1998 |
| WO | WO 01/93656 | 12/2001 |
| WO | WO 02/39890 | 5/2002 |
| WO | WO 02/069781 | 9/2002 |
| WO | WO 2004/012579 | 2/2004 |
| WO | WO 2005/018494 | 3/2005 |

OTHER PUBLICATIONS

Palma, "Readjustable Transobturator Sling, A Novel Sling Procedure for Male Urinary Incontinence," Urologia Internationalis, 73:354-356, Dec. 2004.

Bauer et al., The self-anchoring transobturator male sling to treat stress urinary incontinence in men: a new sling, a surgical approach and anatomical findings in a cadaveric study, BJU Int. vol. 95(9), pp. 1364-1366, 2005.

Pereya, "A Simplified Surgical Procedure for the Correction of Stress Incontinence in Women," West J. Surg., Obstetrics & Gynecology, pp. 223-226, Jul.-Aug. 1959.

Compression of the bulbar urethra by transobturator suburethral tape, Progres en Urologie, (abstract), 14(4) pp. 507-511, Sep. 2004.

D. Dargent et al., Pose d'un ruban sous uretral oblique par voie obturatrice dans le traitement de l'incontinence urinaire feminine, Gynecol. Obstet. Fertil., 30:576-582 (2002).

Moir J., et al., "The Gauze-Hammock Operation," The Journal of Obstetrics and Gynaecology of the British Commonwealth, vol. 75, No. 1, pp. 1-9, Jan. 1968.

Dietz et al., "Mechanical Properties of Urogynecologic Implant Materials," 14, 239-243 (2003).

Iglesia et al., "The Use of Mesh in Gynecologic Surgery," 8:105-115 (1997).

* cited by examiner

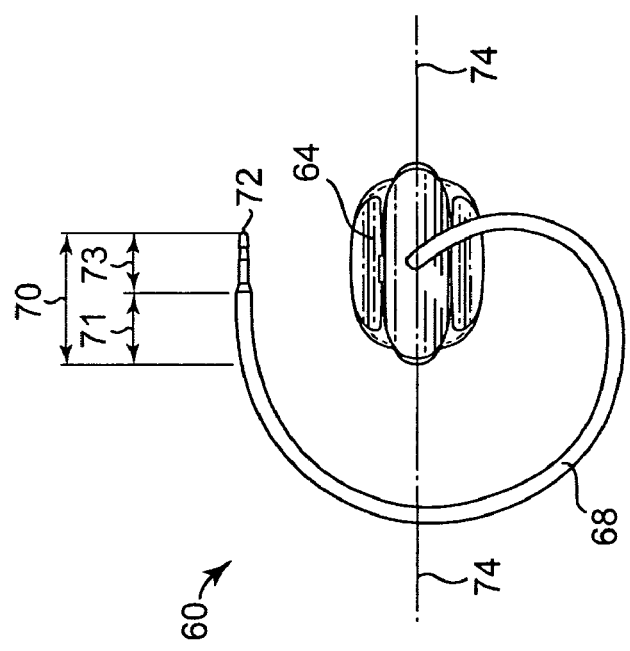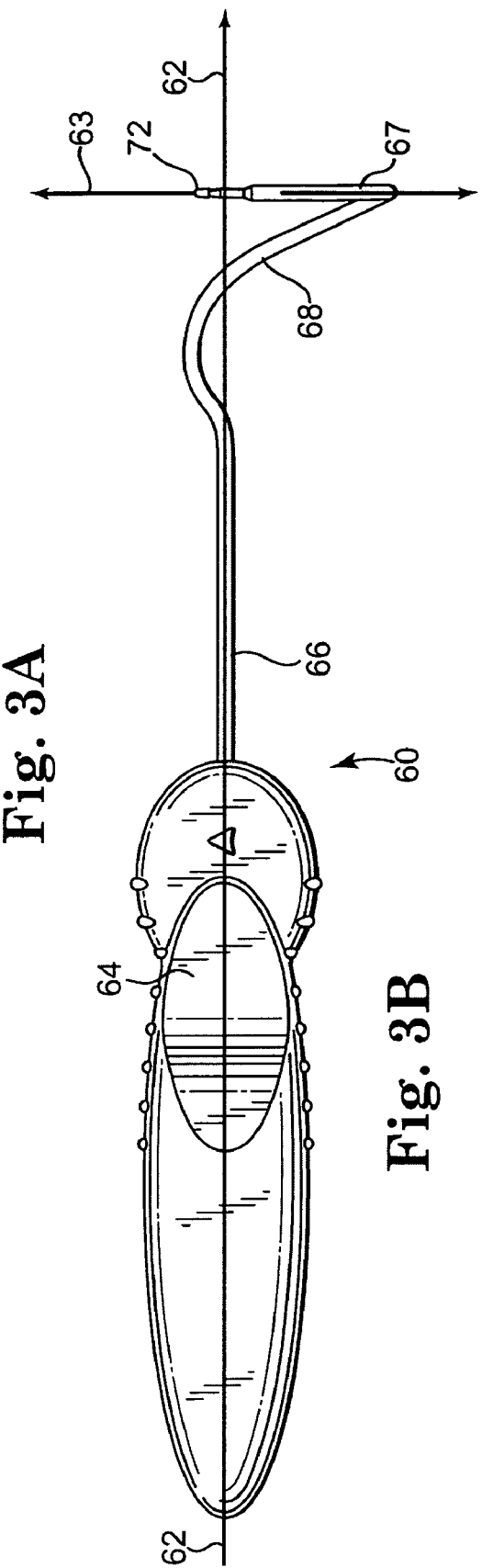
Fig. 3A
Fig. 3B

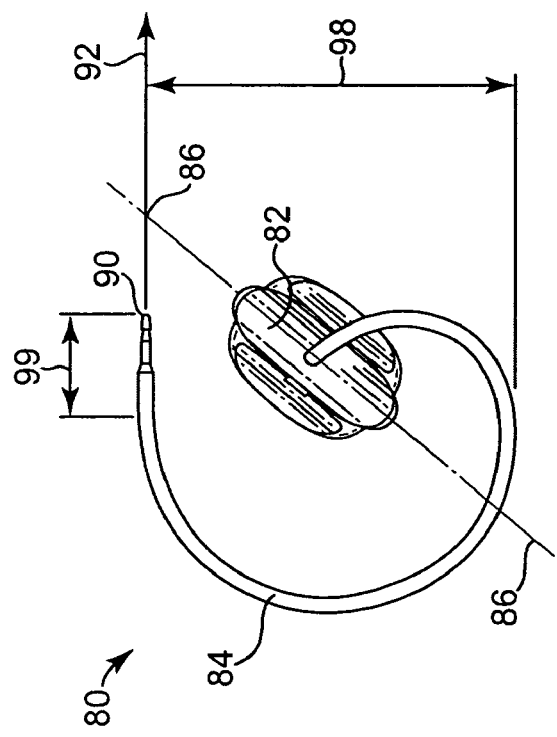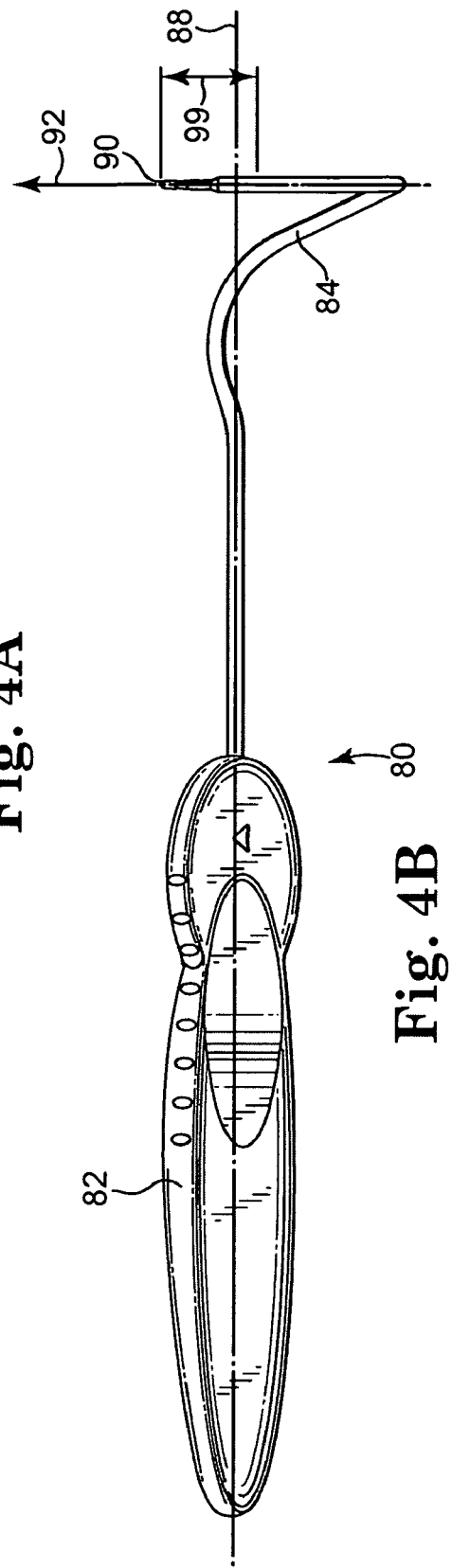
Fig. 4A
Fig. 4B

NEEDLE DESIGN FOR MALE TRANSOBTURATOR SLING

PRIORITY CLAIM

The present non-provisional patent application claims priority under 35 USC §119(e) from U.S. Provisional Patent Applications having U.S. Ser. No. 60/650,208, filed on Feb. 4, 2005, by Arnal et al., and titled TRANSOBTURATOR SLING FOR MEN; U.S. Ser. No. 60/650,209, filed on Feb. 4, 2005, by Arnal et al., titled TRANSOBTURATOR SLING FOR MEN; U.S. Ser. No. 60/659,714, filed on Mar. 8, 2005, by Arnal et al., titled NEEDLE DESIGN FOR MALE TRANSOBTURATOR SLING; U.S. Ser. No. 60/659,504, filed on Mar. 8, 2005, by Arnal, titled NEEDLE DESIGN IMPROVEMENTS FOR MALE TRANSOBTURATOR SLING; U.S. Ser. No. 60/677,457, filed on May 4, 2005, by Hauschild et al., titled URETHRAL SLING OF KNITTED MESH WITH EDGE TREATMENT; U.S. Ser. No. 60/683,185, filed on May 20, 2005, by Arnal, titled TRANSOBTURATOR SURGICAL SLING DELIVERY SYSTEM AND METHOD; and U.S. Ser. No. 60/650,207, filed on Feb. 4, 2005, by Rehder et al, titled TRANSOBTURATOR SLING FOR MEN, wherein the entirety of said provisional patent applications are incorporated herein by reference.

FIELD OF THE INVENTION

The invention relates to surgical tools, surgical implant, and related systems and surgical methods.

BACKGROUND

Urinary incontinence is a significant health concern worldwide. In the urology field, needles, suture passers, and ligature carriers, are used in a variety of procedures, many of which are designed to treat incontinence. Examples of such surgical instruments include Stamey needles, Raz needles, and Pereyra needles. See Stamey, *Endoscopic Suspension of the Vesical Neck for Urinary Incontinence in Females*, Ann. Surgery, pp. 465-471, October 1980; and Pereyra, *A Simplified Surgical Procedure for the Correction of Stress Incontinence in Women*, West. J. Surg., Obstetrics & Gynecology, pp. 243-246, July-August 1959.

A pubomedial sling procedure involves placement of a surgical implant in the form of a urethral sling to stabilize or support the bladder neck or urethra, to treat incontinence. There are a variety of different sling procedures. Descriptions of different sling procedures are disclosed in U.S. Pat. Nos. 5,112,344; 5,611,515; 5,842,478; 5,860,425; 5,899,909; 6,039,686; 6,042,534; 6,110,101; 6,478,727; 6,638,211; PCT Publication Nos. WO 02/39890 and WO 02/069781.

Some pubomedial sling procedures extend a sling from the rectus fascia in the abdominal region to a position below the urethra and back again to the rectus fascia. Although serious complications associated with sling procedures are infrequent, they do occur. Complications include urethral obstruction, prolonged urinary retention, bladder perforations, damage to surrounding tissue, and sling erosion.

The Tension-free Medial Tape (TVT) procedure (available from Ethicon, of N.J.) uses a Prolene™ nonabsorbable, polypropylene mesh. Problems with the TVT procedure are documented in the literature and patents. Problems associated with the TVT procedures and the like are acknowledged and described in PCT publication nos. PCT WO 00/74613 and PCT WO 00/74594; U.S. Pat. Nos. 6,273,852; 6,406,423; 6,478,727; 6,638,210; 6,652,450; 6,612,977; and 6,802,807.

A cadaver study indicated that the TVT needle is placed in close proximity to sensitive tissue such as superficial epigastric vessels, inferior epigastric vessels, the external iliac vessel and the obturator. See, Walters, Mark D., *Percutaneous Suburethral Slings: State of the Art*, presented at the conference of the American Urogynecologic Society, Chicago (October 2001) and PCT International Publication No. WO 02/26108.

Additional sling procedures are described in U.S. Pat. No. 6,478,727 and PCT Publication Nos. WO 02/39890 and WO 02/069781.

A significant percentage of pubomedial sling procedures are conducted after previous pelvic surgery. A pubomedial sling procedure can be particularly challenging if the patient has scarring as a result of previous pelvic surgery or other anatomical problems. The additional complications presented by significant scarring present surgeons with a greater surgical challenge and may lead some surgeons to forego an otherwise beneficial sling procedure. Unfortunately, this reduces a patient's options for treating incontinence.

U.S. Pat. No. 6,638,211 describes an implantable device or tape for use in correcting urinary incontinence. The tape includes sprayed polypropylene fibers that result in a strong implantable device. The tape also has a silicone-coated portion and tapered free ends. The procedure uses an Emmet needle that includes an eyelet. To create the eyelet, the distal portion of the Emmet needle is enlarged. A surgical procedure using an Emmet needle is believed to be described in the French publication D. Dargent, S. Bretones, P. George, and G. Mellier, *Pose d'un ruban sous uretral oblique par voie obturatrice dans le traitement de l'incontinence urinaire feminine*, Gynecol. Obstet. Fertil. 2002; 30: 576-582.

In the procedure described in U.S. Pat. No. 6,638,211, an incision is made in the perineal skin facing the obturator and in the groin. The Emmet needle is first inserted through the cutaneous incision. The Emmet needle is first introduced perpendicular to the perineum for about 15 mm (passing through the internal obturator muscle as far as just outside the ischiopubic branch). The Emmet needle is then allowed to describe its curvature. The free end of the tape is then slipped into the eyelet of the needle. The needle and tape connection is thus reversible as one merely needs to unthread the tape from the eyelet to separate the tape from the needle. Separation of the tape and needle while both are within the body is undesirable as it would require the needle to be repassed through the body. The needle with the tape extending through the eyelet is then pulled back though the skin incision. The eyelet and threaded tape present a sudden discontinuity encountered by the tissue that can make tape and needle passage inconvenient and unnecessarily irritative or traumatic to tissue. Additionally, the final placement of the sling may not be optimum in this procedure.

There is ongoing research and development of new or improved medical procedures for treating incontinence. A recent development in treating incontinence in men and women is the use of a transobturator tissue path for placement of a urethral sling. New and potentially useful and improved surgical tools, slings, kits and systems are developed within this surgical subject matter.

SUMMARY

The invention relates to novel three-dimensional surgical tools and related methods for treating pelvic conditions including incontinence.

The tool comprises a handle portion and a needle portion with a distal region that has structure in three dimensions.

Unlike the Emmet needle of the prior art, the inventive instrument has substantial structure in three dimensions. This three-dimensional needle portion is sized and shaped to extend between a "lateral" incision substantially adjacent the patient's obturator foramen at the inner thigh, and a "medial" incision that is located lateral from and substantially parallel to the "lateral" incision, e.g., an external incision in the perineal region in a male or an intravaginal incision in a female.

Exemplary needles can include a spacer extending from the handle, the spacer extending along a longitudinal axis shared with the handle and the tool. At the end of the spacer begins a three-dimensional region of the needle that may be of any three-dimensional form useful for extending between incisions as described, curved or angular in three-dimensions, and which may include portions that are in the form of a helix, partial or variable helix, or a spiral.

The needle portion can also have structure near the needle distal end, at the distal end of the three-dimensional region, for associating the needle with a component or portion of an implantable material for treating the incontinence such as a urethral sling. The structure for associating the instrument with an implantable material can comprise an eyelet or a dilator or other structure.

There are many vulnerable, sensitive pelvic anatomical structures and tissues in the region of the obturator foramen, including the pudendal artery (internal), the pudendal canal (Alcock), and nerves (e.g. the perineal and labial). The needles of the invention are preferably sized and shaped to pass through the obturator foramen along a path that is substantially free of vascular and nerve structures, either in men or women. The size and shape of the needles help avoid the sensitive structures. The tip of the needle is preferably substantially blunt to help avoid damage to the sensitive structures. Alternatively, the tip may be slightly sharpened to assist in the initial passage of the needle.

The invention relates to different features of the tool, including various dimensions of the handle, spacer, and three-dimensional region, and various spatial relationships between these features of the tool.

In certain tool embodiments, the handle portion, when viewed along the longitudinal axis, is non-circular and includes a larger dimension or width. This width dimension defines a midplane of the handle when viewed along the longitudinal axis.

Certain embodiments of the invention relate to the relative position of the needle distal end (which refers to the far end or tip of the three-dimensional portion) relative to this midplane when the tool is viewed along the longitudinal axis. In general, the needle distal end can be placed at an angle from the midplane to provide the user of the tool with an ergonomic advantage in allowing optimal force, sensitivity, and control of the tip when holding the handle using the midplane. The particular angle can depend on the type of procedure for which the tool is designed.

The tool can be used to install various surgical implants, such as implants used to treat conditions of the pelvic region in men and women, an example being a urethral sling.

The invention also contemplates surgical kits or assemblies for treating a pelvic condition such as incontinence. The assembly includes a surgical instrument as described, having a handle portion and a needle having substantial structure in three dimensions. The needle portion has a portion that is sized and shaped to extend between an incision substantially adjacent a patient's obturator foramen and a medial incision (in either direction). The assembly may also include an implantable article such as a urethral sling. Exemplary slings may be prepared from an implantable synthetic material and a sheath situated about the implantable synthetic material. A needle may optionally include structure for associating the needle with the implant. The assembly may further including a dilator for connecting the implant to the needle. Alternately, a needle may comprise an eyelet for that purpose.

When the assembly includes a dilator, the dilator preferably has engagement surfaces for connecting the dilator to the instrument. The dilator is preferably operatively associated with the sheath and implantable material. The structure of the needle portion in a distal region comprises surfaces complementary with the engagement surfaces of the dilator for resisting separation of the instrument from the dilator once the two are engaged.

The needle portion can optionally be sized and shaped for a predetermined side of a patient, and the handle portion can include indicia indicating the predetermined side of the patient, direction of rotation during use in a surgical procedure, etc.

The invention also contemplates a surgical assembly comprising at least one surgical tool, e.g., a first surgical instrument for use on a right side of a patient. The first surgical instrument comprises a handle portion and a needle portion having substantial structure in three dimensions and a distal region. The needle portion has a portion that is sized and shaped to extend between an incision substantially adjacent the obturator foramen on the patient's right side and a medial incision (this needle may be referred to as a "left" hand tool because it may be held by a surgeon during use with the surgeon's left hand). The assembly also has a second surgical instrument for use on a left side of a patient (sometimes referred to as the "right" hand tool). The second surgical instrument comprises a handle portion and a needle portion having substantial structure in three dimensions and a distal region. The needle portion of the second instrument has a portion that is sized and shaped to extend between an incision substantially adjacent the obturator foramen on the patient's left side and a medial incision.

The assembly may also include an implant, such as a urethral sling comprising implantable knitted polypropylene material and a sheath situated about the implantable synthetic material. The first and second surgical instruments may include an eyelet for receiving a suture to tie the surgical instrument to the implantable material. Alternatively, the assembly can have first and second dilators for associating the first and second surgical instruments with the implantable material.

The invention also contemplates various methods for treating incontinence using surgical implantation tools as described herein, including "transobturator" methods in men and women that include a tissue path that traverses the obturator foramen.

An exemplary method comprises steps of creating a medial incision, creating an incision substantially adjacent the patient's obturator foramen, providing an elongate surgical instrument comprising a needle having substantial structure in three dimensions, providing an implant for treating the incontinence, passing the three dimensional region of the needle between the incisions, then associating the implant with the instrument, and passing the implant through tissue and through the patient's obturator foramen using the instrument. Preferably, the step of providing an elongate surgical instrument includes the step of providing an instrument with a portion that is substantially helically shaped, and the step of passing the implant through tissue includes the step of passing the implant along a substantially three-dimensional or helical path. The step of providing a surgical instrument preferably includes the step of providing an instrument with an elongate handle portion having an axis, and the step of passing the instrument between the incisions preferably includes the step of rolling the instrument about the axis of the handle portion.

In another aspect, the method comprises the steps of creating a medial incision, creating an incision substantially adjacent the patient's obturator foramen, providing an elongate surgical instrument comprising a handle portion, a needle portion having an extension portion projecting from the handle portion and a variable spiral portion with a distal end, providing an implant for treating the incontinence, passing at least a portion of the variable spiral portion between the incisions by initially passing the distal end through the incision substantially adjacent the patient's obturator foramen and then through the medial incision, then associating the implant with a portion of the instrument that has emerged from the medial incision, and then moving the distal region of the instrument with the implant associated therewith from the medial incision toward the patient's obturator foramen to pass the implant through tissue. Optionally, the step of associating the implant with a portion of the instrument that has emerged from the medial incision includes the step of using a suture to tie the implant to an eyelet in the distal region of the needle.

In yet another aspect, the method comprises the steps of creating a medial incision, creating an incision substantially adjacent the patient's obturator foramen, providing an elongate surgical instrument comprising first and second regions, providing an assembly having an implant for treating incontinence, initially passing the first region of the instrument initially through the medial incision toward the incision substantially adjacent the patient's obturator foramen in a path through the patient's obturator foramen until the first region of the instrument emerges from the incision substantially adjacent the patient's obturator foramen, leaving the second region of the needle projecting from the medial incision, then associating the second region of the instrument that projects from the medial incision with the assembly, and then moving the instrument out of the patient's body to pass the implant through tissue from the medial incision toward the incision substantially adjacent the patient's obturator foramen to place the implant in a therapeutically effective position.

Another aspect of the invention relates to a surgical instrument for implanting an implantable material to a pelvic region. The instrument includes: a handle having a longitudinal axis and an elongate width dimension normal to the longitudinal axis, the elongate width dimension defining a midplane; and a needle portion extending from the handle along the longitudinal axis. The needle includes a spacer portion connected to the handle; a three-dimensional region connected to the spacer portion distal from the handle, and having structure in three dimensions; and a needle distal end at the distal end of the three-dimensional region. The needle portion is sized and shaped to extend between an incision substantially adjacent to a patient's obturator foramen, through the obturator foramen, and to a medial incision. The needle distal end is located at an angle between 20 to 70 degrees from the midplane (when viewed along the longitudinal axis).

Another aspect of the invention relates to a surgical instrument for implanting an implantable material to treat incontinence. The instrument includes: a handle and a needle extending from the handle. The needle includes a spacer portion connected to the handle, a three-dimensional region connected to the spacer portion distal from the handle, and has a structure in three dimensions that includes a needle distal end at the distal end of the curved portion. The needle portion is sized and shaped to extend between an incision substantially adjacent to a patient's obturator foramen, through the obturator foramen, and to a perineal incision. The three-dimensional region has a length in the range from 2.3 to 5 inches and a diameter in the range from 2.3 to 5 inches. An axis of the needle end portion lies within a plane that is orthogonal to the longitudinal axis of the tool.

In another aspect the invention relates to a method of performing a surgical procedure. The method includes a step of rotating a surgical instrument having a handle comprising a midplane, about a longitudinal axis. A surgical instrument is provided that includes a handle and a functional section that engages with tissue, a surgical implant, or a surgical instrument. The handle includes an elongate dimension defining a midplane. The functional section is engaged with one or more of tissue, a surgical implant, and a surgical instrument. The handle is grasped with the midplane approximately parallel to the palm. The handle is rotated using the hand such that during the rotation the handle rotates at least ninety degrees, and during ninety degrees of the rotation the hand traverses ninety degrees between a forty-five degree open palm and a forty-five degree closed palm.

BRIEF DESCRIPTION OF THE DRAWINGS

FIGS. 3A and 3B are views of a surgical needle that include features of the invention as described.

FIGS. 4A and 4B are views of a surgical needle that include features of the invention as described.

Figure 1A:
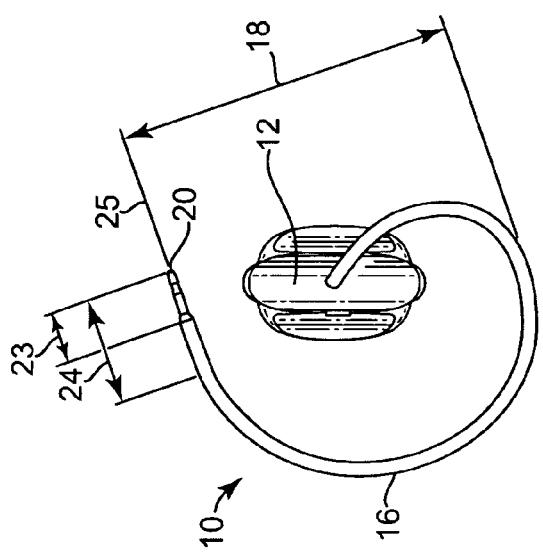
FIGS. 1A and 1B are views of a conventional surgical needle.

All figures are schematic and not necessarily to scale.

DETAILED DESCRIPTION

The invention is directed to surgical tools and related methods useful for treating pelvic floor disorders such as incontinence or stress urinary incontinence (SUI) in both men and women. The invention is also directed to surgical kits and systems that involve the surgical tools and methods.

The invention includes methods of treating urinary incontinence by surgical implantation of a urethral sling, through a tissue path that traverses the obturator foramen, in men and women. These "transobturator" methods generally involve two lateral incisions, each at a right and left inner thigh of a patient, near a patient's obturator foramen, and a third "medial" incision that can be at the perineal region for men or at a vagina for women. The medial incision can be an external incision in the perineal region in a male, and can be an intravaginal incision in a female. An elongate urethral sling is installed to be located between the medial incision and the two lateral incisions with opposing end portions of the sling traversing each obturator foramen. See, e.g., Assignee's copending United States Patent Application Publication US2003/0171644 (U.S. Ser. No. 10/306,179) filed Nov. 27, 2002, and entitled "Transobturator Surgical Articles and Methods," and U.S. Ser. No. 11/347,047, entitled "Transobturator Methods for Installing Sling to Treat Incontinence, and Related Device," filed on even date herewith, the entirety of each of these being incorporated herein by reference.

Transobturator methods can involve dissection one or more tissue path, typically one on each of the patient's left and right sides between the lateral incision and the medial incision, by way of the obturator foramen. Three-dimensional tools described herein can produce these tissue paths in either direction. An "outside-in" approach dissects the tissue path by initiating the dissection at the lateral incision and proceeding through the obturator foramen in the direction of the medial incision. An outside-in approach generally will include a next step of attaching an end portion of an implant to the needle distal end and retracting the needle back through the tissue path in a direction opposite the direction of dissection to pull the end portion of the implant back through the tissue path.

An "inside-out" approach uses an opposite direction of dissection, initiating the dissection at the medial incision and proceeding through the obturator foramen in the direction toward the lateral incision. An inside-out approach may require alternate steps to install the end portion of the implant, such as attaching an implant at the handle end of the tool (after removal of the handle), and pulling the end portion of the implant through the tissue path in the direction from the medial incision to the lateral incision. Other alternatives are also useful, such as attaching the implant end portion to the leading edge of the surgical tool (at the needle distal end) before dissection, and pushing the end portion through the tissue path at the same movement of the dissection. As yet another alternative the tissue path can first be dissected, the needle can be removed (retracted), an end portion of an implant can be associated with the needle distal end, and the needle and end of an implant can be re-passed through the tissue path from the medial incision to the lateral incision.

The invention involves tools useful in any of these transobturator procedures, or others. The tools include a handle portion ("handle") and a needle portion extending from an end of the handle. The handle can normally be elongate and define a longitudinal axis of the tool. The handle is optional and may be removably attached to the needle, or it may be repositionably attached to the needle (such as for an "inside-out" approach that removes the handle and attaches an end portion of the implant at the trailing end of the tool to pull the end portion through a dissected tissue path). Alternatively, the handle may be permanently attached to the needle. Suitable handles are described, for example, in U.S. Provisional Patent Application Nos. 60/347,494, 60/336,884, and 60/343,658.

Exemplary needle portions extend from the handle starting with a straight "spacer" portion that extends from the handle along the longitudinal axis of the tool, i.e., along a longitudinal axis shared with the handle. At the end of the spacer distal from the handle the needle includes a three-dimensional region. The three-dimensional region features a shape and size in three dimensions that is designed to allow the three-dimensional region to extend between a medial incision and a lateral incision, in one direction or the other or in either direction.

An exemplary needle can have dimension and shape features sufficient to extend from a lateral incision adjacent the anterior side of the pubic bone, through the obturator foramen portion of the pubic bone, to a position on the posterior side of the pubic bone, and to then emerge from a medial incision made between the patient's obturator foramen incisions. Alternately, a needle may be shaped to extend along the same tissue path in the opposite direction, entering at the medial incision and exiting at the lateral incision. A large number of different sizes, shapes, and dimensions of needles are suitable for the present invention.

Various portions of a tool, including handle, spacer, and three-dimensional region, can include various inventive features or combinations of inventive features related to shape, size, material, or dimensions of any of these components, or relative size or spatial relationships between one portion of the tool and another portion of the tool. Any of the individual features may be useful according to the described invention, and any of the features may also be useful in combination (including any possible combination of features) with in any one or more of the other features described herein.

A three-dimensional region and a spacer can have any dimensions or combination of dimensions to provide a tool useful for implanting a pelvic implant, e.g., a urinary sling, using a transobturator method. The length of a spacer can provide a desired distance between a handle and the three-dimensional region of a tool. Exemplary length dimensions of a spacer portion of the instrument, along a longitudinal axis of the device between a handle and a beginning of a three-dimensional region, can be from 0 to 3 inches, typically from 1 to 2.5 inches.

Another dimension of an inventive tool is the cross-sectional diameter of the needle, which can be the same or different along the length of the needle, but is generally a uniform dimension along the spacer and three-dimensional region of a needle. The needle portion (spacer and distal three-dimensional, e.g., helical, region) can be of a generally rigid material such as a metal or rigid plastic, and can have a generally circular cross section. For an exemplary needle made of stainless steel (e.g., 17-4PHH900), a cross-sectional diameter of the needle portion, including the spacer and the three-dimensional region, can be in the range up to 5 mm, e.g., a diameter in the range from 3 to about 4 mm, such as a range that includes 0.125".

A three-dimensional region of a needle can include a curved or angular formation that may be a full or partial helix, a variable helix, a spiral, or the like, in three-dimensions. The three-dimensional region may include regions that are straight, angular (e.g., cornered), or curved optionally with increasing or decreasing radius. The three-dimensional region can be considered to include components that include a proximal portion of the three-dimensional region generally starting at the end of the spacer and extending to a needle end portion. The "needle end portion" includes: (1) a "needle distal end," which is the very end or tip at the far distal end of the needle; and, (2) a "needle end portion" is also considered to include an amount of the terminal length of the needle at the distal end such as the terminal inch of needle length adjacent to the needle distal end.

A needle end portion according to various embodiments of the tools described herein may be either straight or curved, or partially straight and partially curved. As an example, the terminal inch of the needle may exhibit a curve that approximates or matches a curvature of the proximal region of the three-dimensional region of the needle, extending to the needle distal end. Alternately, the terminal inch may include approximately ½ inch of curved needle and a terminal ½ inch that is straight. This terminal ½ inch may be an optional "engaging surface" or "securement surface" for engaging a portion of an implant, and may be straight or curved.

For example, a three-dimensional region of a needle can include an engaging portion that exhibits no curvature, i.e., the engaging portion can be straight for a desired distance at the end of the needle leading to the needle distal needle end or "tip," when the needle is viewed along the longitudinal axis of the tool. A straight engaging portion may be used for engaging a straight plastic dilator at an end of an implant. An exemplary straight engaging portion can be straight for a distance that extends from the tip of the needle to a distance of 10 mm, e.g., up to 20 mm, from the needle distal end along the needle proximally toward the handle, at which point the three-dimensional region of the needle begins a curve in the form of a helix, spiral, or the like. Alternately, the engaging portion may be curved, e.g., along an arc that matches the three-dimensional region of the needle. A curved engaging portion or needle end portion may be desirable to allow the needle distal end to dissect a curved path while the axis of the needle end portion is aligned with the tissue path being dissected; this may reduce trauma during dissection.

Embodiments of the invention also relate to an "axis of the needle end portion," which is a line projecting from the needle distal end. The axis of the needle end portion can be tangent to the needle at the needle distal end for a curved needle end portion, and can be a line defined by the needle end portion including the needle distal end for a needle end portion that includes a terminal straight portion.

Also, in combination with other dimensions described herein, embodiments of the invention can relate to a radial distance from the longitudinal axis of the tool to the needle distal end. Exemplary radial distances between a longitudinal axis and needle distal end may be from 0.5 to 2 inches. For a tool designed for use with a male anatomy, an exemplary distance may be from 0.7 to 1.7 inches, e.g., from 0.9 to 1.5 inch. For a tool designed for use with a female anatomy, an exemplary distance may be from 0.5 to 1.6 inches, e.g., from 0.7 to 1.3 inch.

A three-dimensional region can exhibit a length along the longitudinal axis of the tool that is particularly suitable for a specific surgical procedure, such as a male transobturator installation of a urethral sling. This length of the three-dimensional region (e.g., spiral or helix), can be the length measured along the longitudinal axis of the tool from the beginning of the three-dimensional region (e.g., starting at the end of a spacer) to the most distal extent of the needle, typically the needle distal end. Exemplary lengths of the three-dimensional region can be in the range from about 1.5 inches and to about 3 inches, depending on the procedure and anatomy. Exemplary lengths of the three-dimensional region for a tool designed for use on the female anatomy can be in the range from about 1.5 inches and to about 2.5 inches, such as from 1.75 to 2.25 inches. Exemplary lengths of the three-dimensional region for a tool designed for use on the male anatomy can be in the range from about 2.25 inches and to about 3 inches, e.g., from 2.25 to 2.75 inches.

Another feature of a three-dimensional region of a needle, which can be useful either alone or with other features described herein, is the diameter (or "width") of the three-dimensional region. The three-dimensional region can have a diameter or "width" that is preferably great enough to allow for passage of the three-dimensional region through a desired tissue path as described herein such as a path around the inferior pubic ramus and through the natural opening of the pubic bone, while also being small enough to avoid sensitive structure in this region of the body. A diameter or "width" of a three-dimensional region can be measured as the distance from a line through an axis of the needle end portion, to a parallel line through a far opposing side of the three dimensional portion of the needle, when viewed along the longitudinal axis of the tool handle (see, e.g., FIG. 1A). Exemplary diameters for the three-dimensional region for a tool can be in the range from about 1.25 inches and to about 5 inches, depending on the procedure and anatomy. Exemplary width of a three-dimensional region such as a helix as defined, for use in female transobturator methods may be, e.g., in the range from 1.25 inches to less than 3 inches, such as from 2 inches to 2.25. To accommodate transobturator methods of installing pelvic implants in a male anatomy, a diameter may be generally larger than prior helical tools useful for implanting urethral slings. Exemplary diameters of a three-dimensional region such as a helix as defined, designed specifically for use in male transobturator methods may be, e.g., in the range from 2 inches to 5 inches, such as from 2 inches to 4 inches, e.g., from 2 to 3 inches.

Still another feature of a three-dimensional region of a needle that can be useful alone or with other features described herein, can be that the needle end portion of the three-dimensional region can lie within (or define) a line or a plane that is perpendicular to or orthogonal to the longitudinal axis of the handle or the tool when the tool is viewed from the side. This means that the needle end portion, when the tool is viewed from a side perspective, can define a line that is substantially perpendicular to the longitudinal axis of the handle, the handle and spacer, or the tool. The line will not intersect the axis but when viewed from a side of the tool will be at ninety degrees. Alternately, the needle end portion (e.g., if curved) can define a plane that is substantially orthogonal to the longitudinal axis of the handle, the handle and spacer, or the tool. This feature may be particularly useful for tools designed for the male anatomy, because a needle end portion that is perpendicular to the longitudinal axis may assist in avoiding the male prostate during use to dissect a transobturator tissue path.

Described differently, a three-dimensional region of a needle can follow a path that lengthens as the needle defines a length and curvature extending away from the handle or spacer to form a curved three-dimensional region. After defining a desired length-wise and desired shaped of a three-dimensional needle extending a distance from the handle along the longitudinal axis of the handle, the needle may continue to extend in length but without extending a further distance from the handle along the longitudinal axis. This may define a line or a plane that can be viewed to be perpendicular or orthogonal to the axis of the handle. A desirable effect is that the three-dimensional region of the needle can be sized and shaped to define a curved tissue path between a medial and a lateral incision (in either direction) that avoids contacting sensitive tissue, particularly with a male anatomy. In specific, by placing an axis of the needle end portion of the three-dimensional region in a line or plane that is perpendicular or orthogonal to the axis of the handle, as described, the needle may define a tissue path that avoids the male prostate. For example, a desired length of the needle end portion that is within this plane may be a terminal 1 inch, e.g., terminal 2 inches, for a tool designed to be used on the male anatomy. (The needle end portion may still be straight or curved).

In addition to features of the various portions of a tool, including the handle, needle spacer, and needle three-dimensional region, the invention also contemplates specific features of the handle portion and the relation between the handle portion and one or more different components of the tool, such as the three-dimensional region of the needle, which features can be used alone or in combination with any one or more other features related to the particular shapes, sizes, material, or dimension of any the handle, spacer, or three-dimensional region of the needle.

In certain embodiments of tools of the invention, a handle or a portion of the length of a handle may exhibit a non-circular form when viewed along the longitudinal axis of the handle. The non-circular cross-section can be, e.g., an oval, rectangle, rhombus, etc., having one dimension (e.g., maximum dimension), a "width," that is greater than the dimension perpendicular to that "width." The non-circular form will provide one or more surfaces on the handle for a surgeon to place pressure onto and to achieve a grip. The non-circular cross-sectional form also defines a midplane that is a plane that includes the longitudinal axis of the handle and extends along the width or the widest dimension of the handle when viewed in cross section along the longitudinal axis.

Tools described herein may include a needle distal end that is located at any useful position relative to a midplane and a longitudinal axis of a handle of the tool. An angle between the needle distal end and a midplane can be defined as the angle between the needle distal end and the midplane when the tool is viewed along the longitudinal axis, viewing in the direction looking at the three-dimensional region of the tool, with the longitudinal axis of the tool taken as an origin for purposes of defining the angle. This view is illustrated in FIGS. 7A, 7B, 8A, and 8B, among others.

According to embodiments of the invention, a needle distal end of a tool (measured at the tip of the needle distal end) may be located at a position in space relative to the handle midplane and longitudinal axis, to provide the user with an ergonomic advantage. The ergonomic advantage may relate to useful or optimized (e.g., increased) amounts of force and control that can be applied at the needle distal end during an installation procedure, meaning amounts of force, sensitivity, and control that the user will have over the needle distal end when manipulating the handle using the midplane for leverage or grasping. As an example, a needle distal end may be located at an angle relative to the midplane to provide an ergonomic strength advantage or control advantage to a surgeon during particularly risky or sensitive portions of a surgical procedure, such as portions of a surgical procedure that involve using the needle distal end to dissect a tissue path through or near sensitive organs or tissues, e.g., traversing the obturator foramen. The angle between the needle distal end and the midplane may provide the surgeon with the use of maximum hand or wrist strength and maximum control and precision during manipulation of the needle distal end through a sensitive or risky tissue path, when applying pressure to a handle having a midplane.

In more detail, when the human hand holds an instrument having a handle, using the palm, fingers, and thumb (as in FIGS. 7A, 7B, 8A, and 8B), and rotates the handle about an axis that approximately lines up with an axis of the wrist and forearm, the human hand and wrist exhibit different amounts of strength and control (precision of control) depending on the rotational orientation of the hand and wrist relative to the forearm. When the forearm is held horizontally and the hand holds a handle of a surgical tool having a midplane, with the longitudinal axis situated horizontally along the palm, the wrist (i.e., hand, wrist, and forearm) can exert the greatest amount of force and control to the handle when the palm of the hand is oriented vertically and within a range of positions from 45 degrees past vertical in either direction (i.e., "opened" or "closed" up to 45 degrees from a vertical palm). As used herein, an "open" hand or wrist posture refers to a posture of a user's hand held with an approximately horizontal forearm with the palm off of vertical (e.g., 45 degrees from vertical) in a direction that places the palm in a direction facing upward from horizontal (e.g., 45 degrees up or open from vertical) (see FIGS. 7B and 8B); a "closed" hand or wrist posture refers to a posture of a user's hand held with a horizontal forearm, with the palm off of vertical (e.g., 45 degrees from vertical) in a direction that places the palm in a direction facing downward from horizontal and the user may partially view the back of the hand; (see FIGS. 7A and 8A).

The vertical palm posture is most natural for the hand, and 45 degrees past vertical in either an opened or a closed direction will be sufficiently near the natural vertical position to provide a range of maximum or optimal control and strength for manipulating a handle having a midplane. According to embodiments of the invention, a handle midplane and needle distal end can be positioned relative to each other so that when rotating the tool to for use in a surgical procedure (e.g., to install a surgical implant), movement of the user's hand will include rotational movement of the hand within the ninety degree range of motion (within the range up to 45 degrees on either side of a vertical palm) that provides maximum control and strength, particularly during sensitive, risky, or control-critical steps of an installation procedure. The relative positions of a midplane and needle distal end, including angles and distances, can be selected for any particular surgical procedure, and may be different for different surgical procedures, e.g., for particular tissue paths or different directions of a tissue path being dissected.

A relatively sensitive portion of a transobturator procedure, in a male or female, can involve dissecting a tissue path connecting a lateral incision and a medial incision while traversing the obturator foramen. The lateral incision is near the patient's obturator foramen. The medial incision may be near the perineum in a male, such as between the corpus spongiosum and the corpus cavemosum, or at or near a vaginal incision in women. The tissue path can be dissected in either direction, using an "inside-out" or an "outside-in" technique. For an "outside-in" approach the tissue path can be initiated by positioning the needle distal end at a lateral incision; the tool is rotated to cause the needle distal end to enter the lateral incision and then to traverse the obturator foramen; and the tool is rotated further to cause the needle distal end to exit the tissue path at a location at or near a medial incision. For an "inside-out" dissection, the tissue path is initiated by insertion of the needle distal end at the medial incision, the tool is rotated to cause the needle distal end to traverse the obturator foramen, and the tool is further rotated to cause the needle distal end to exit at the lateral incision.

The step of dissecting a tissue path between a lateral and a medial incision, in either direction, requires training and high sensitivity and control of the needle distal end of the surgical tool, using the handle, to avoid damaging sensitive structures such as nerves or other organs within and near the obturator foramen, and also to guide the needle distal end to a desired exit position. The tissue path can be traversed using a needle as described herein, with rotation of the handle over a range of at least ninety degrees, generally somewhat greater than ninety degrees. According to embodiments of the invention, the tool can be designed so that rotation of the tool handle to cause the needle distal end to define and traverse this tissue path occurs by rotating the user's wrist through a range that includes the ninety degree range of motion through which the wrist exhibits maximum control and strength.

In specific embodiments, a handle having a midplane can allow improved leverage (e.g., torque) and control when applying force from the handle to the needle distal end. A handle midplane can be oriented relative to a needle distal end so the user has maximum control and strength through approximately 90 degrees of motion traversed in using the needle distal end to dissect a tissue path between a lateral incision, through an obturator foramen, and to a location at or near a medial incision (or through the same tissue path in the opposite direction). The particular angle may differ depending on factors such as the type of procedure that the tool is used for, the tissue path, and the direction of movement of the three-dimensional region of the needle when defining a tissue path.

For a three-dimensional tool designed for a male or female transobturator procedure, the relative orientations of the handle midplane and the needle distal end can position the needle distal end at the starting point of a tissue path that traverses the obturator foramen, while the user's hand is positioned at or near the beginning of the ninety-degree range of maximum wrist strength and control and the user's palm is at least forty-five degrees opened or closed from vertical (e.g., 50 or 55 degrees opened or closed from vertical, or even up to 80 or 90 degrees from vertical). For an outside-in procedure, the needle distal end may be positioned at a starting point that places the needle distal end at an entry of a lateral incision; for an inside-out procedure, the needle distal end may be positioned at a starting point that places the needle distal end at an entry of a medial incision.

Another feature that can be incorporated into a tool as described herein to improve ergonomics and provide improved strength and control of a needle distal end by manipulation of a handle having a midplane, is the relation between a handle midplane and an axis of the needle end portion. This angle can be defined when viewing the tool along the longitudinal axis, looking at the end of the tool that includes the three-dimensional portion, e.g., as in FIGS. 7A, 7B, 8A, and 8B. An axis of a needle distal end can be a line or tangent defined by the needle at the needle distal end when the tool is viewed along the longitudinal axis.

According to embodiments of the invention, an axis of the needle end portion can be oriented relative to a handle midplane so that the needle distal end can be rotated to define a tissue path that traverses the obturator foramen with favorable ergonomic control and strength, and with ease of passage of the needle distal end and reduced trauma to tissue. For example, the axis of the needle end portion may preferably be approximately tangential to a circle about the longitudinal axis of the tool at the radius of the needle distal end. For a curved needle end portion, a line tangent to the needle distal end can be tangent to a circle having an origin at the longitudinal axis, or at an angle that is up to 5, 10, or 15 degrees from tangent. Placing the needle end portion or needle distal end at or near a tangent of a circle having a radius defined by the needle distal end, can place the axis of the needle end portion or needle distal end in line with the direction of advancement of the needle distal end, during rotation, to allow the needle distal end to be pointing in the direction of advancement of the needle distal end when creating a tissue path; stated differently, the needle distal end can be relatively perpendicular to tissue as the needle distal end is rotated to dissect tissue and define a curved tissue path.

Another optional feature useful in combination with the described angles between a needle distal end, axis of needle distal end, and a handle midplane, can be a radial distance from the longitudinal axis of the tool to the needle distal end (tip), which provides desired utility or an ergonomic advantage.

Figure 7A:
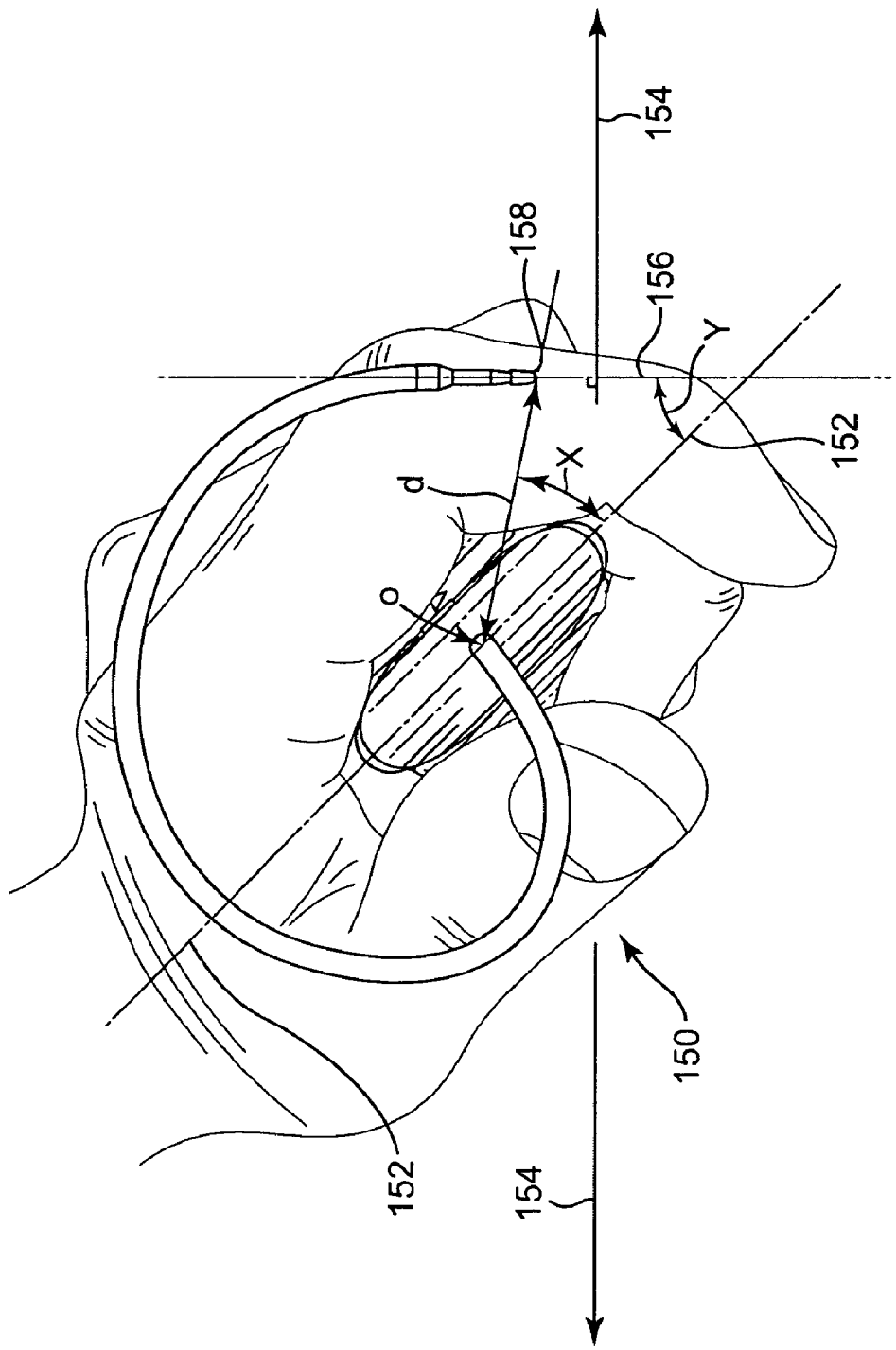
FIGS. 7A and 7B are views of a surgical needle during exemplary use and movement.
Figure 7B:
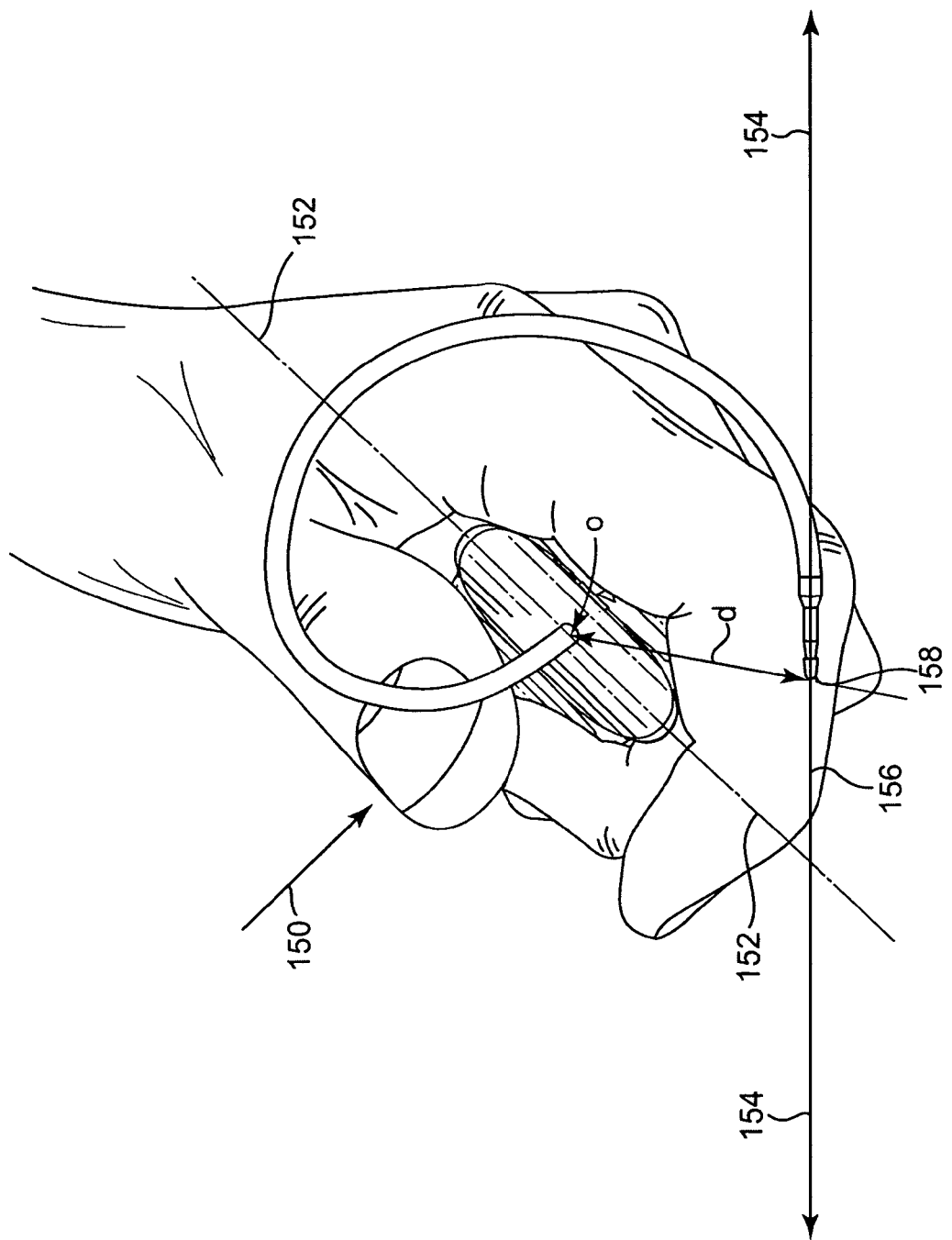

FIG. 7A shows left-handed tool 150 (for use on a patient's right side) held by a user's left hand, and for use to form a tissue path using an outside-in tissue dissection technique. Handle midplane 152 is oriented approximately 45 degrees from horizon 154. Axis 156 of needle distal end 158 is about ninety degrees from horizon 154, meaning that axis 156 is approximately vertical as the needle distal end will enter a lateral incision, and makes an angle of approximately 45 degrees with midplane 152 (angle Y). Distance d represents the radial distance from a longitudinal axis of tool 150 to distal end 158. From the illustrated orientation the user will rotate the left hand and the tool counterclockwise (from the user's perspective, clockwise as illustrated) to dissect and define a tissue path traversing the obturator foramen. The needle distal end traverses forty-five degrees as the hand rotates counter-clockwise and partially opens to a vertical hand orientation. The needle distal end traverses another forty-five degrees past vertical as the hand opens further, for a total of ninety degrees through a range of motion that includes hand and wrist motion of maximum strength and control. During this movement the needle distal end (158) traverses the obturator foramen. At the end of the movement or shortly thereafter, needle distal end 158 will be located at a position near a medial incision at the vagina in a female or at a perineal location in a male. FIG. 7B shows the hand and tool orientation after the tool has been rotated ninety degrees.

FIGS. 7A and 7B show an operator using a left hand to operate a left-handed tool, e.g., to install a portion of an implant at a patient's right side. The ergonomic advantages of the design of left-handed tool 150 would also apply if the user were to instead use his or her right hand to operate the left-handed tool of FIGS. 7A and 7B, for installing a portion of an implant in a patient's right side. In that embodiment, the right hand would start by holding the handle of tool 150 with the tool in the same orientation is shown in FIG. 7A. The tool handle midplane would be at the same 45-degree orientation from horizon 154 but the user would hold the tool with the right hand instead of the left hand. In a surgical setting the right hand may be crossed in front of the surgeon's body. The right hand, however, would hold the handle with a right hand posture that is approximately 45 degrees from vertical in an open posture. The right hand would rotate 45 degrees to approximately a palm-vertical posture, and would finish the rotation through 45 degrees to place the right hand and wrist at a 45 degree closed posture, or beyond.

Figure 8A:
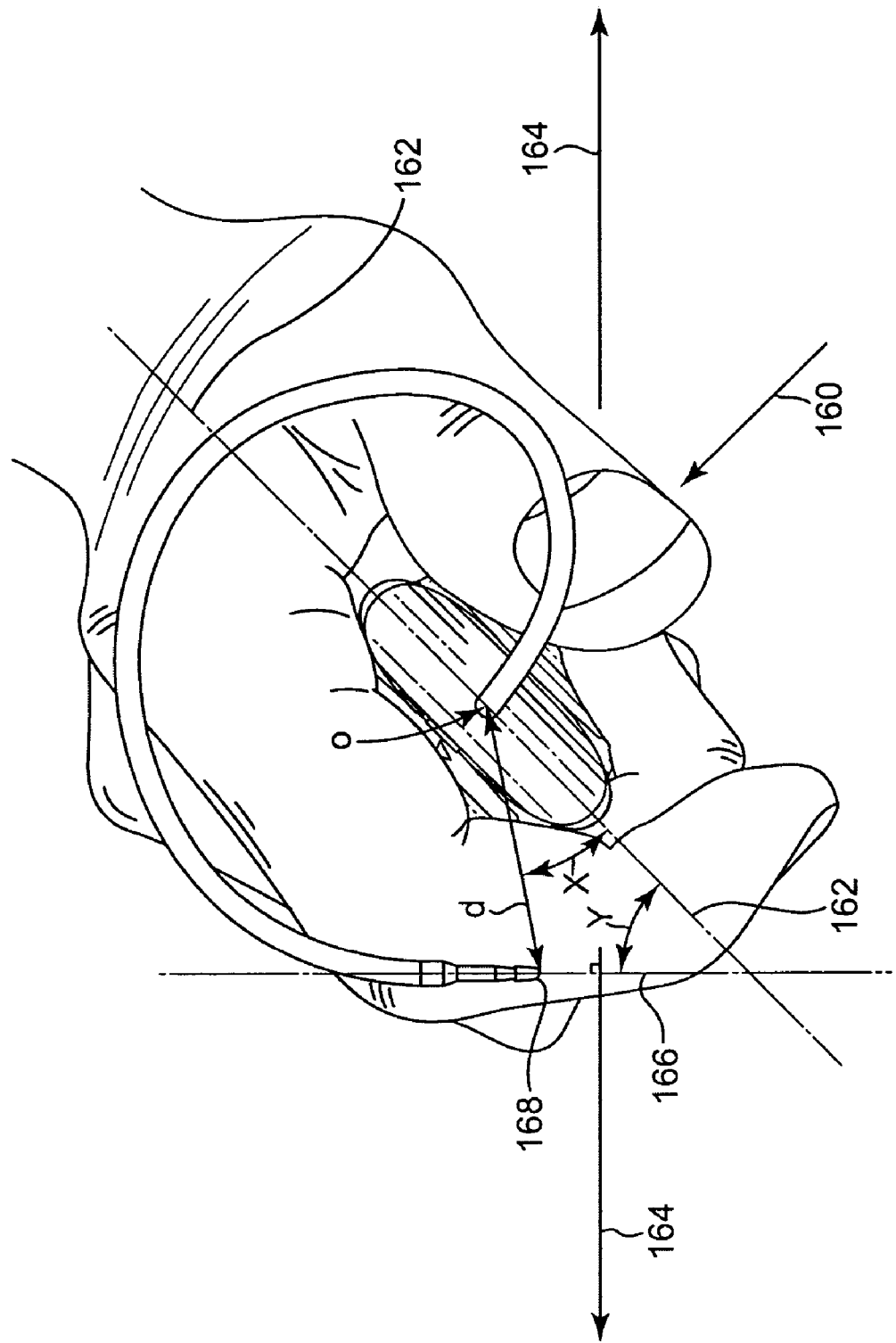
FIGS. 8A and 8B are views of a surgical needle during exemplary use and movement.
Figure 8B:
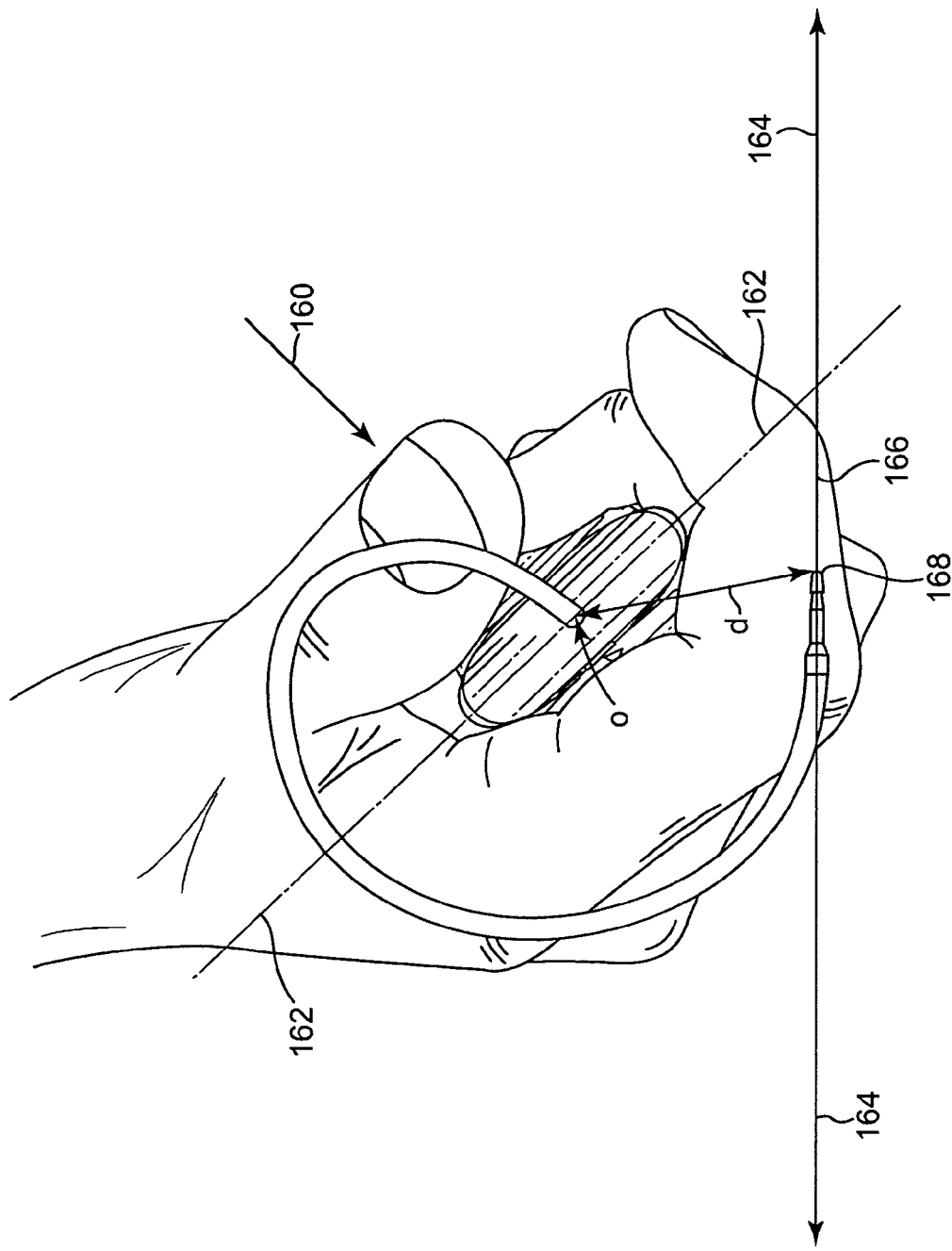

FIGS. 8A and 8B illustrate a right-handed tool for use in installing a portion of an implant on a patient's left side using an outside-in tissue dissection approach. Tool 160 is held by a user's right hand with handle midplane 162 oriented approximately 45 degrees from horizon 164. Axis 166 of needle distal end 168 is about ninety degrees from horizon 164, meaning that axis 166 is approximately vertical as the needle distal end will enter a lateral incision, and makes an angle of approximately 45 degrees with midplane 162 (angle Y). From the illustrated orientation, the user will rotate the right hand and the tool clockwise from the user's perspective, counter-clockwise as illustrated, to dissect and define a tissue path traversing the obturator. The needle distal end traverses forty-five degrees as the right hand rotates clockwise and partially opens to a vertical hand orientation. The needle distal end traverses another forty-five degrees past vertical as the hand opens further, for a total of ninety degrees through a range of motion that includes hand and wrist motion of maximum strength and control. During this movement needle distal end 168 traverses the obturator foramen. At the end of the movement or shortly thereafter the needle distal end will be located at a position near a medial incision at the vagina in a female or at a perineal location in a male. FIG. 8B shows the hand and tool orientation after the tool has been rotated ninety degrees.

Specific angles and dimensions between a needle distal end and a midplane can depend on features of a tool design such as the intended surgical procedure that the tool will be used for and the type of anatomy (male or female). For a tool use to dissect a tissue path using an "outside-in" technique (see, e.g., FIGS. 7A and 7B) the three-dimensional portion may generally consist of a curved needle originating from a longitudinal axis of the tool, e.g., at a spacer. When viewed along the axis from the end at the three-dimensional region as in FIG. 7A, and with midplane 152 representing a Cartesian x-axis, the needle starts from the origin (O) moving initially in a direction having a tangent approximately in a downward direction along the negative y axis. The needle lengthens with a clockwise rotation (from this view) to define an increasing-radius spiral or helix that makes a pass through at least 180 degrees around the x and y axes, and up to or optionally exceeding 270 degrees, e.g., from 200 to 250 degrees, such as from 220 to 245 degrees or from 230 to 240 degrees. According to embodiments of the invention, when viewed as described, a needle distal end of such a left-handed tool for an outside-in procedure may terminate at a location that is in the first quadrant of Cartesian coordinates. As illustrated at FIG. 7A, angle "X" between needle distal end 158 and midplane 152 (with origin at the tool longitudinal axis) can be from 20 to 70 degrees, preferably from 25 to 50 degrees, e.g., from 30 to 40 degrees. This angle X as shown in FIG. 7A is a positive angle with the needle distal end being located within the first quadrant of Cartesian coordinates. Optionally and preferably, the radial distance (d) from the longitudinal axis (origin, "O") to needle distal end 158 can be in the range from 0.5 to 2 inches, e.g., from 0.7 to 1.7 inch for a male tool, e.g., from 0.5 to 1.6 inches for an exemplary female too. Also optionally, for an outside-in transobturator procedure, angle Y between midplane 152 and axis 156 of needle distal end 158 can be in the range from about positive 30 to 60 degrees, such as from positive 40 to 50 degrees, or from positive 42 to 48 degrees, in the first or third quadrant of Cartesian coordinates. For a tool designed for an "inside-out" procedure, the magnitude of the angles would be similar (i.e., 30 to 60 degrees, etc.,) but a needle end portion would be located below the x-axis of a Cartesian system in the third or fourth quadrant, e.g., depending on whether the tool is a left-hand or a right-hand tool; the angles may be considered to be "negative" angles of the same magnitude. See FIG. 2C.

For a right-handed tool as in FIGS. 8A and 8B the dimensions and angles would be similar except in a mirror-image of the left-handed tool of FIGS. 7A and 7B. Distance d and angles X and Y have the same values but lie in different quadrants of a Cartesian coordinate system. With midplane 162 taken as the x-axis of a Cartesian system, as illustrated, needle distal end 168 is located in the second quadrant, with angle Y still being positive.

Figure 1B:
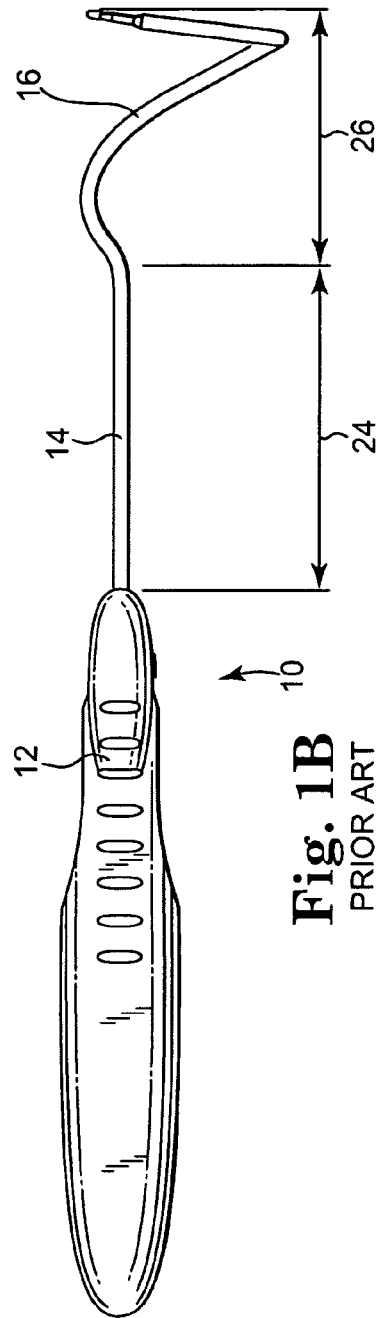

FIGS. 1A-1B illustrate two views of a prior art tool used to install a urethral sling by a transobturator method, e.g., with female anatomy. FIG. 1A illustrates a view of tool 10 along a longitudinal axis of the tool. FIG. 1B illustrates a side view of tool 10. Tool 10 includes handle 12 and a needle extending longitudinally from an end of the handle along the longitudinal axis of the handle. The needle includes spacer 14 and three-dimensional region 16 which may be considered to be a helix or a spiral. The diameter 18 of three-dimensional region 16 is measured from the axis 25 of needle distal end 20, to a parallel line through the far side of the three-dimensional region. The length of spacer 14 is indicated as length 24 between the end of handle 12 and the beginning of three-dimensional region 16. The length of three-dimensional region 16 is indicated as length 26. The illustrated embodiment of a tool includes straight needle end portion 24, which includes a straight end portion having a length of approximately the terminal 0.75 inch of the needle. Needle end 24 as illustrated is straight, including a straight engaging portion 23, which is about 0.5 inches.

Figure 2A:
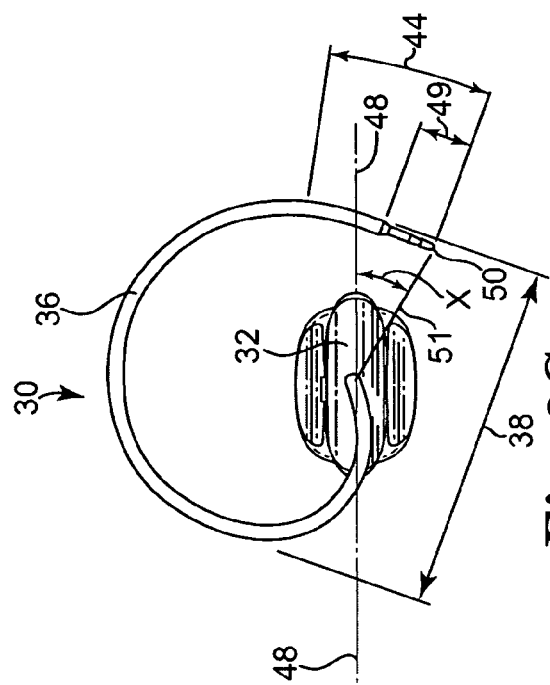
FIGS. 2A, 2B, and 2C, are views of a surgical needle that include features of the invention as described.
Figure 2C:
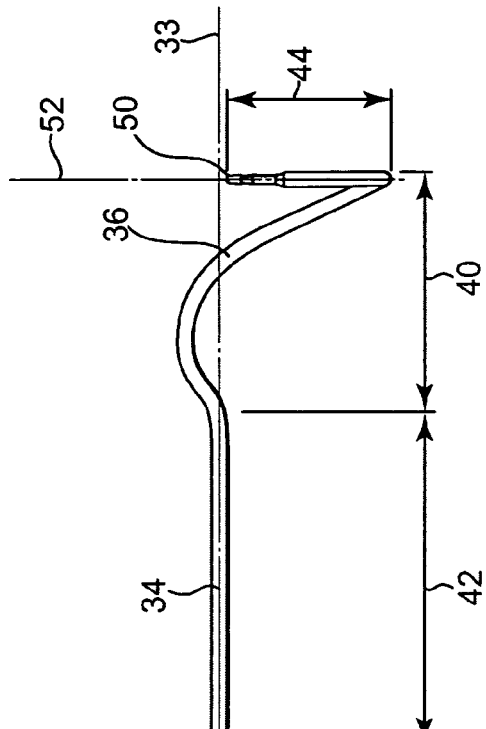
Figure 2B:
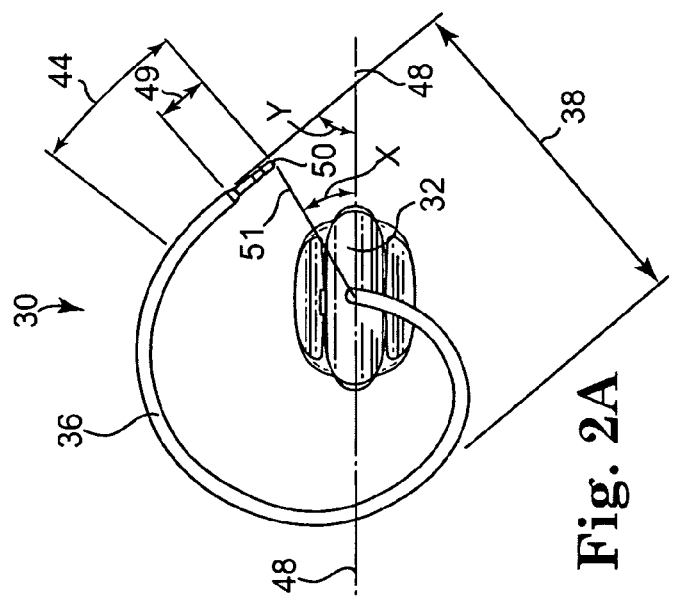

FIGS. 2A and 2B illustrate two views of a tool that includes features according to the invention. FIG. 2A illustrates a view of tool 30 along a longitudinal axis of the tool. FIG. 2B illustrates a side view of tool 30. Tool 30 includes handle 32 and a needle extending longitudinally from an end of handle 32 along longitudinal axis 33 of the handle and tool. The needle includes spacer 34 and three-dimensional region 36 which may be considered to be a helix, a variable helix, or a spiral, etc. Diameter 38 can be as desired for either a male or female procedure. For a male transobturator design, diameter 38 can be larger than diameters of relevant prior art tools, and may be, for example, in the range from 2 to 5 centimeters, e.g., about 2.4 inches. Length 42 of spacer 34 can be any desired length; for installing a urethral sling in male anatomy by a transobturator tissue path, a preferred length 42 can be, for example, in the range from 1 to 5 inches, e.g., from 1.75 to 2.25 inches. Length 40 of three-dimensional region 36 can be any desired length, and for a male transobturator procedure may preferably be in the range from 2.25 to 5 centimeters, e.g., from 2.4 to 2.5 inches. Angle Y is approximately 45 degrees, and angle X is approximately 30 degrees. Using these angles to provide an ergonomic advantage for an outside-in transobturator installation procedure, the dimensions such as width and length of the three-dimensional region may be smaller or larger, while still achieving an ergonomic advantage for a male or a female anatomy. Smaller dimensions can be useful if the tool is being designed for a procedure on the female anatomy.

Other inventive features are also illustrated in FIGS. 2A and 2B. For instance, needle end portion 44, which includes a length of about one inch at the end of the needle, is curved up until engaging portion 49, which is straight. This differs from needles that include a straight portion leading up to and adjacent to an engaging portion, such as the prior art needle shown in FIGS. 1A and 1B.

Also illustrated in FIGS. 2A and 2B is an inventive feature related to the positioning of needle distal end 50 relative to midplane 48 of handle 32. Needle distal end 50 is located relative to midplane 48 to allow an ergonomic advantage by a surgeon during an outside-in transobturator installation procedure, which involves improve torque or strength applied to handle 32 when inserting an implant using the needle. When tool 30 is viewed along the longitudinal axis from the distal end of tool 30, looking in a direction from the distal end toward the proximal end, needle distal end 50 is located at an angle of about 30 degrees from midplane 48 (angle X).

Also illustrated in FIG. 2B is the feature of an axis of needle end portion line 52 or plane defined by the distal end portion that is substantially orthogonal to the longitudinal axis of handle 32. Distal end portion 44 can define either a line or a plane, depending on, e.g., whether the distal end portion is straight or curved. In FIG. 2A, distal end portion 44 includes a curve, and as such defines a plane including needle distal end 50. This plane, illustrated as line 52, is substantially orthogonal to the longitudinal axis of tool 30.

Radial distance 51 of tool 30 can be as desired and as described herein, and may differ for a female transobturator tool compared to a male transobturator tool. An exemplary radial distance for a female tool may be from 0.5 to 1.6 inches, and for a male tool may be from 0.7 to 1.7 inches.

FIGS. 2A and 2B illustrate a tool designed for an inside-out approach. A tool with similar features, designed for an inside-out method of creating a tissue path, is shown at FIG. 2C (having number designations similar to those of FIG. 2A). FIG. 2C illustrates a tool for use in a transobturator procedure on a patient's left side (using a surgeon's right or left hand); the needle distal end lies in the fourth quadrant. A tool for use in a transobturator procedure on a patient's right side would include a needle distal end that lies in the third quadrant. Either tool can preferably include an angle X that is a "negative" angle relative to midplane 48 (that places needle distal end 50 below midplane 48 when viewed as illustrated, in the range from 20 to 70 degrees, e.g., from 25 to 50 degrees, or from 30 to 40 degrees.

FIGS. 2A and 2B illustrate a handle midplane angled differently relative to the needle distal end, compared to the orientation shown in FIG. 1A. FIGS. 3A and 3B illustrate a needle according to another embodiment of the invention wherein the needle distal end is about parallel with the handle midplane. Additionally, the straight portion at the needle end portion of tools 30 and 60 extends along the engaging portions 49 and 73, respectively, of the needles, and not proximally beyond those engaging portions, as compared to the tool of FIG. 1A, which includes a straight portion 24 of the needle proximal to an engaging portion 23. The overall diameter of the three-dimensional regions of the needles of the tools illustrated at FIGS. 2A, 2B, 3A, or 3B, can be selected based on specific procedures and anatomy, and may be prepared for use with male or female anatomy.

FIGS. 3A and 3B illustrate a surgical needle that includes other features of inventive tools described herein. FIG. 3A illustrates a view of tool 60 along a longitudinal axis 62. FIG. 3A illustrates a side view of tool 60. Tool 60 includes handle 64 and a needle extending longitudinally from an end of the handle along longitudinal axis 62 of the handle. The needle includes spacer 66 and three-dimensional region 68 which may be considered to be a helix, variable helix, a spiral, etc. Tool 60 includes needle end portion 70, which includes a length of approximately 1 inch at the end of the needle, including engaging portion 71 adjacent to needle distal end 72. According to the embodiment of FIGS. 3A and 3B, the overall diameter of three-dimensional region can be larger when compared to relevant prior art needles, especially for a tool 70 designed for use with a male transobturator procedure. Also, as illustrated, needle end portion 70 defines a plane or a line (63) that falls within a plane that is orthogonal to longitudinal axis 62. Tool 60 includes needle end portion 70, which includes a curved portion (71) and a straight engaging portion (73), ending at needle distal end 72. Needle end portion 70, including engaging portion 73, is approximately parallel to midplane 74 of handle 64. Three-dimensional region 68, except for engaging portion 73, does not include any other portion that is straight.

FIGS. 4A and 4B are various views of yet another surgical needle, 80, having handle 82, three-dimensional region 84, midplane 86, longitudinal axis 88, needle distal end 90, and line or plane 92 defined by needle end portion 99. Needle end portion 99 is illustrated to include a curved portion 97 and a straight engaging portion 95. Tip 90 is at an angle of about 25 degrees from midplane 86 to allow improved torque during use. Optionally, in particular for use in male transobturator procedures, the diameter, length, or both of three-dimensional region 84 can be larger than conventional needles, such as a width 98 of about 2.3 to 2.6 inches and a length of about 2.3 to 2.6 inches. As illustrated, a plane that includes axis 92 of needle end portion 94 is orthogonal to longitudinal axis 88.

Figure 5A:
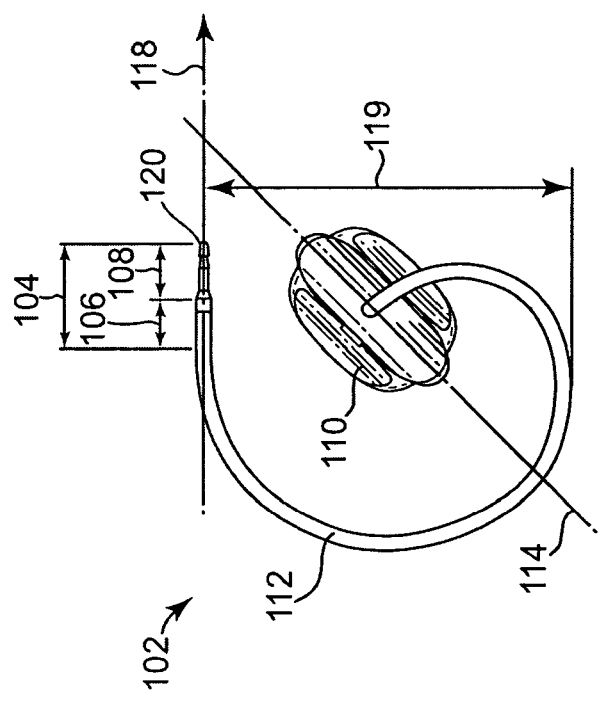
FIGS. 5A and 5B are views of a surgical needle that include features of the invention as described.
Figure 5B:
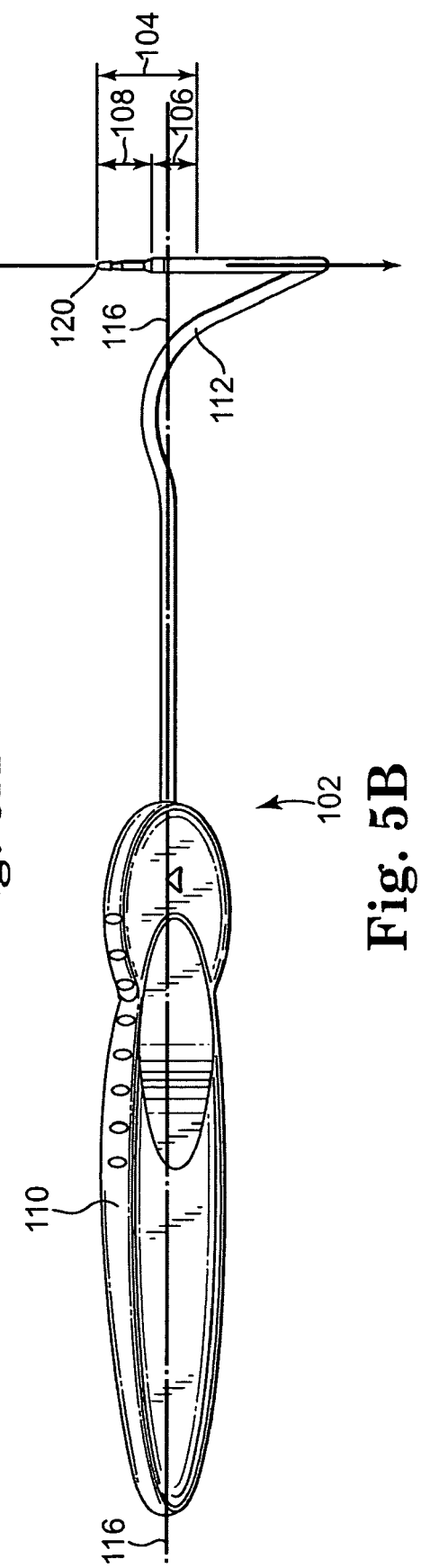

According to another embodiment of the invention, FIGS. 5A and 5B are various views of another inventive surgical needle wherein the handle is positioned relative to the needle distal end to provide an ergonomic advantage for the user, and wherein there is a flat (i.e., straight) section near the needle distal end. FIGS. 5A and 5B illustrate surgical needle 102 having handle 110, three-dimensional region 112, midplane 114, longitudinal axis 116, needle distal end 120, width 119, and line 118 defined by needle end portion 104. Needle end portion 104 includes straight or flat needle portion 106 and straight engaging portion 108. Needle distal end 120 is located radially from axis 116 at an angle of about 25 degrees from the midplane 114 to allow improved torque during use. Optionally, the diameter, length, or both of three-dimensional region 112 can be larger than conventional needles, such as a diameter of about 2.4 inches and a length of about 2.4 to 2.5 inches. As illustrated, line 118, defined by straight needle end portion 104, lies within a plane perpendicular to longitudinal axis 88 when viewed from a side of tool 110, e.g., as in the side view of FIG. 5B. Line 118 is not in the same plane as axis 116 and does not intersect axis 116.

Figure 6A:
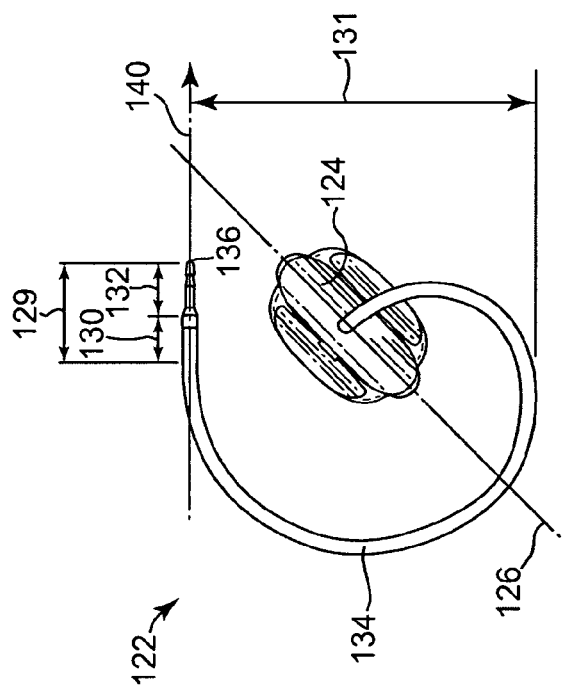
FIGS. 6A and 6B are views of a surgical needle that include features of the invention as described.
Figure 6B:
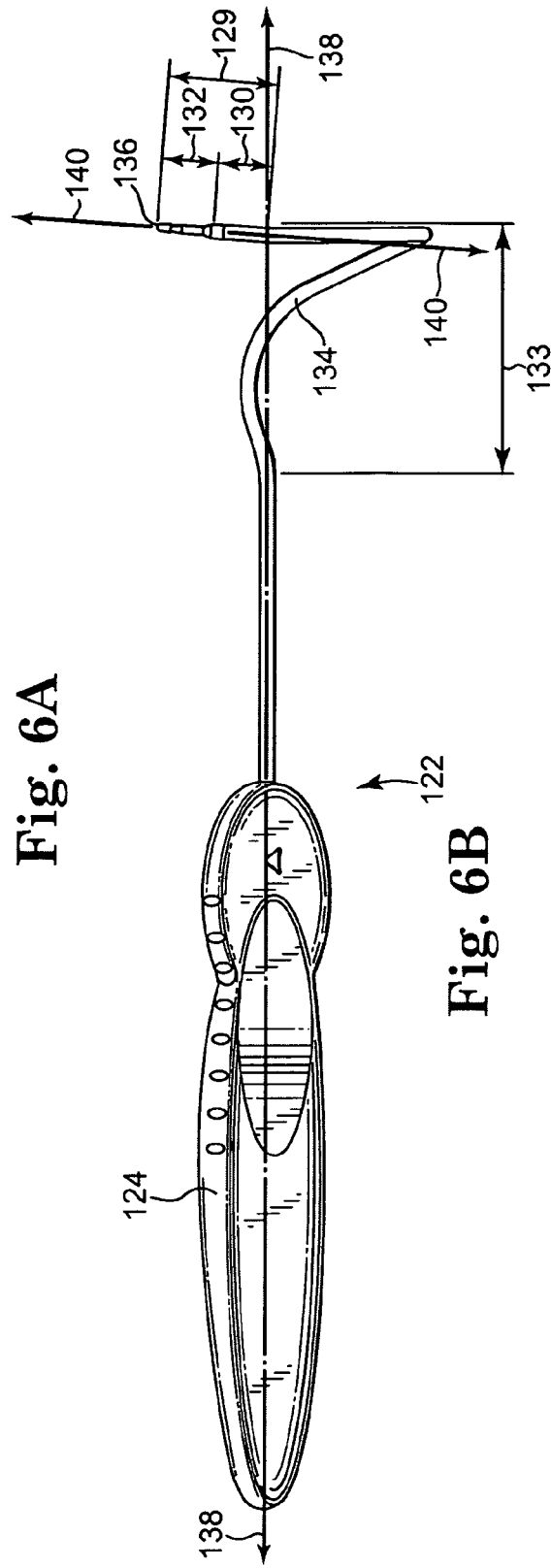

FIGS. 6A and 6B illustrate yet another surgical needle. Features of this embodiment include an axis 140 of a needle distal end that is bent away from the handle (as in FIG. 1A), optionally a diameter of the three-dimensional region that is for either a male or a female anatomy. FIGS. 6A and 6B illustrate views of a surgical needle wherein the handle is positioned relative to the needle distal end to provide an ergonomic advantage for the user, and wherein there is a flat (i.e., straight) section 130 of the three-dimensional portion of the needle, near needle distal end (when viewed along the axis), in accordance with another aspect of the invention. FIGS. 6A and 6B illustrate surgical needle 122 having handle 124, three-dimensional region 134, midplane 126, longitudinal axis 138, needle distal end 136, and line 140 defined by needle end portion 128. Needle end portion 128 includes straight or flat portion 130 and straight engaging portion 132, each of which is straight (not curved) when viewed along longitudinal axis 138. Needle distal end 136 is at an angle of about 25 degrees from midplane 126, to allow improved torque during use. Optionally, the diameter, length, or both of three-dimensional region 134 can be for male or female procedures; for male procedures length 133 and diameter or width 131 can be larger than conventional needles, such as a diameter of about 2.4 inches and a length of about 2.3 to 2.6 inches. As illustrated, line 140, defined by axis of straight needle end portion 113, is slightly angled to and not perpendicular or orthogonal to longitudinal axis 138, e.g., when view from a side of tool 122, e.g., as in the side view of FIG. 6B. Line 140 is not in the same plane as axis 138 and does not intersect axis 138.

The needle of a tool can be made of a durable, biocompatible surgical instrument material such as, but not limited to, stainless steel (e.g., 316 stainless steel or 17-4 stainless steel), titanium, Nitinol, polymers, plastics and other materials, including combinations of materials. The needle should have sufficient structural integrity to withstand the various forces (e.g. forces caused by dilator attachment, and penetration/passage of the needle through the various tissues) without undergoing any significant structural deformation. Optionally, the needles could be sufficiently malleable to allow a practitioner or user of the device to modify the needle to a desired shape and, thereby, optimize the procedural approach.

Needles may be disposable or reusable (e.g. sterilizable by steam sterilization procedures). In another aspect of the present invention, the needles may be provided in a kit, such as any of the kits described in any of U.S. Pat. Nos. 6,612,977; 6,641,525; 6,652,450; 6,802,807; published U.S. Pat. Application No. 2002-0147382-A1; and U.S. Provisional Application Ser. Nos. 60/263,472, filed Jan. 23, 2001; 60/269,829, filed Feb. 20, 2001; 60/281,350, filed Apr. 4, 2001; 60/295,068, filed Jun. 1, 2001; and 60/306,915, filed Jul. 20, 2001.

One embodiment of kit includes the needle and other needles (not shown, but for example including the needles shown in published U.S. Pat. Application No. US-2002-0099258-A1) designed for placing a sling, under the urethra.

In another aspect of the present invention, a needle may optionally include the capacity to deliver a medicament (e.g. anesthesia) during the surgical procedure. For example, the needle may be hollow with an open end. The needle may have a connector for associating with a medicament reservoir and delivery mechanism (e.g. a syringe).

Needles as described may be used in conjunction with a wide variety of sling materials and sling assemblies. The sling may be integral, monolithic, or a composite of different components or segments of different components. Suitable non-synthetic materials include allografts, homografts, heterografts, autologous tissues, cadaveric fascia, autodermal grafts, dermal collagen grafts, autofascial heterografts, whole skin grafts, porcine dermal collagen, lyophilized aortic homografts, preserved dural homografts, bovine pericardium and fascia lata. Suitable synthetic materials for a sling include polymerics, metals and plastics and any combination of such materials.

Commercial examples of non-absorbable materials include Marlex™ (polypropylene) available from Bard of Covington, RI, Prolene™ (polypropylene) and Mersilene (polyethylene terephthalate) Hernia Mesh available from Ethicon, of New Jersey, Gore-Tex™ (expanded polytetrafluoroethylene) available from W. L. Gore and associates, Phoenix, Ariz., and the polypropylene sling available in the SPARC™ sling system, available from American Medical Systems, Inc. of Minnetonka, Minn. Commercial examples of absorbable materials include Dexon™ (polyglycolic acid) available from Davis and Geck of Danbury, Conn., and Vicryl™ available from Ethicon. Other examples of suitable materials include those disclosed in published U.S. Pat. Application No. 2002/0072694. More specific examples of synthetic sling materials include, but are not limited to polypropylene, cellulose, polyvinyl, silicone, polytetrafluoroethylene, polygalactin, Silastic, carbon-fiber, polyethylene, nylon, polyester (e.g. Dacron) PLLA and PGA. The sling material may be resorbable, absorbable or non-absorbable. Optionally, some portions may be absorbable and other portions may be non-absorbable.

The synthetic slings may be knitted, woven, sprayed or punched from a blank. Some slings may be sufficiently robust to be inserted without a protective sleeve. In other embodiments, some synthetic slings may have an associated protective sleeve to assist with the implantation.

According to certain embodiments, a sling may comprise a mesh material. The mesh material comprises one or more woven, knitted or inter-linked filaments or fibers that form multiple fiber junctions throughout the mesh. The fiber junctions may be formed via weaving, knitting, braiding, bonding, ultrasonic welding or other junction forming techniques, including combinations thereof. In addition, the size of the resultant openings or pores of the mesh may be sufficient to allow tissue in-growth and fixation within surrounding tissue.

As an example, not intended to be limiting, the holes may comprise polygonal shaped holes with diagonals of 0.132 inches and 0.076 inches.

The quantity and type of fiber junctions, fiber weave, pattern, and material type influence various sling properties or characteristics. As another example, not intended to be limiting, the mesh may be woven polypropylene monofilament, knitted with a warp tricot. The stitch count may be 27.5 courses/inch (+ or −2 courses) and 13 wales/inch (+ or −2 wales). The thickness of this example is 0.024 inches. This embodiment of sling is preferably associated with a protective sleeve (described in greater detail below). Non-mesh sling configurations are also included within the scope of the invention.

The sling mesh may be elastic or inelastic. A mesh may be tested to determine whether it is elastic using a series IX Automated Materials Testing System (an Instron), available from Instron Corporation. A 1 cm wide sample of the mesh may be placed in the Instron with a crosshead speed set at 5 in/min and a gauge length of 1 inch. An elastic mesh exhibits at least a 7% elongation under a ½ pound load, more preferably about a 10% elongation under a ½ pound load, and more preferably about 14% under the ½ pound load. An inelastic mesh exhibits less than an 7% elongation under a ½ pound load.

In one example embodiment, the mid-portion of the sling mesh is preferably substantially free of any silicone coatings. In yet another embodiment, the mid-portion of the sling may comprise a non-synthetic material, constructed according to the teachings of U.S. Provisional Patent Appl. No. 60/405,139, filed Aug. 22, 2002.

In another embodiment the sling material may have one or more substances associated therewith through a process such as coating or they may be incorporated into the raw material of the sling. Examples of appropriate substances include, without limitation, drugs, hormones, antibiotics, antimicrobial substances, dyes, silicone elastomers, polyurethanes, radiopaque filaments or substances, anti-bacterial substances, chemicals or agents, including any combinations thereof. The substances may be used to enhance treatment effects, reduce potential sling rejection by the body, reduce the chances of tissue erosion, enhance visualization, indicate proper sling orientation, and resist infection or other effects.

While the slings are preferably rectangular for treating SUI in females and males, other shapes are also contemplated. Depending on the treatment addressed (e.g. to provide hammock support for the bladder or bladder neck, or to address a rectocele or enterocele) the slings may be any of a wide variety of shapes. As an example, the sling may be of the general shape of the slings described and shown in Moir et al., *The Gauze-Hammock Operation*, Journal of Obstetrics and Gynaecology of the British Commonwealth, Volume 75, No. 1, Pps. 1-9 (1968). The size of the sling can take into account the imprecision associated with the range of human anatomy sizes. In a preferred embodiment, the sheath length of the assembly of the present invention is approximately within the range of 10 cm to 50 cm, sheath width is approximately within the range of 1.0 cm to 2 cm, and sheath material thickness is approximately within the range of 0.127 mm to 0.203 mm, respectively. An associated sling has a length, width and thickness approximately within the range of 7 cm to 50 cm; 1.0 cm to 2 cm; and 0.508 mm to 0.711 mm, respectively.

Embodiments of surgical implants that include first and second ends, the implant having a portion that is sized and shaped to extend between at least one incision substantially adjacent the patient's obturator foramen and a medial incision that is lateral from and substantially parallel to the at least one foramen incision. A tool as described herein has a handle at one end, the other end having securement surfaces such as a "dilator" for snap fitting the instrument to another surgical component used to treat incontinence. The snap fit preferably provides a substantially permanent attachment between the instrument and the other surgical component. The instrument and the dilator preferably have complementary engagement surfaces for resisting separation of the instrument from the dilator once they are snap fitted together.

Exemplary implants (e.g., urethral slings) can include a central support portion and "extension" portions (or "end portions"), the central support portion being useful to support a specific type of pelvic tissue such as the urethra, bladder, or vaginal tissue. The central support portion can be sized and shaped to contact the desired tissue when installed, e.g., as a sling, and support the pelvic tissue.

Exemplary implants are described, for example, in Assignee's copending U.S. patent application Ser. No. 11/347,063, entitled "Pelvic Implants and Related Methods, and Ser. No. 11/347,596, entitled "Surgical Implants and Related Methods and Systems," both filed on even date herewith and incorporated herein by reference. These applications describe implants having reinforced edges extensions along edges of end portions, such as by heat treatment of a polymeric (e.g., polypropylene) mesh, and various types of end portions, central support portions, and other features.

Exemplary pelvic implants can include support portions that can include or consist of a central support portion, two elongate end portions extending oppositely from the central support portion, and a load-transfer portion between an end portion and the central support portion. The implant and the support portions of the implant have a lengthwise direction that is considered to be in the direction of the elongate length of the end portions, and a width that is transverse to the lengthwise direction.

Dimensions of an implant can be as desired and useful for any particular installation procedure, treatment, and to support a particular tissue. Dimensions of an exemplary urethral implant for transobturator implantation can be sufficient to allow an end portion to extend from a lateral incision located adjacent to an obturator foramen of a patient, through the obturator foramen, and then to or near a medial incision (e.g., a vaginal incision in a female or a perineal incision in a male). An opposite end portion has sufficient length to extend from the medial incision, through the opposite obturator foramen, and to another lateral incision adjacent to the opposite obturator foramen. Length and width tolerances accounts for a range of human anatomy sizes and for an installation procedure. Lengths of end portions suitable for other methods transobturator methods and variations are also contemplated, such as methods wherein a tissue path does not traverse the obturator foramen, but that extends from the medial incision to the obturator foramen, and the end portion is attached or anchored to the foramen membrane but does not pass through to a lateral incision.

A central support portion can be of sufficient length to support and optionally partially surround a pelvic tissue, e.g., to treat incontinence, such as to support the urethra or urethra-supporting tissue (optionally in combination with some or a portion of the length of load-transfer portions). A width of a central support portion is greater than a width of end portions and is sufficiently wide to increase contact area and frictional forces between a central support portion and a tissue in contact with the central support portion. Exemplary lengths of a central support portion can be in the range from 0.5 to 2 centimeters, such as from 0.7 to 1.8 centimeters. Exemplary widths of a central support portion can be in the range from 1.5 to 4 centimeters, such as from 2 to 4 centimeters. According to implant embodiments, the combined length of two end portions, a central support portion, and one or more load-transfer portion or portions, can be approximately 16 inches (about 41 centimeters), e.g., within the range from 35 cm to 50 cm. Alternate lengths can also be used.

The width of an implant can be as desired and as useful, consistent with the description herein, such as a central support portion that is wider than a width of an end portion. A width of an end portion can be a width useful for implanting the implant and for providing desired strength and fixation properties during and following implantation and optional tensioning of the sling. Typical widths of end portions can be in the range from 0.5 to 2 centimeters, e.g., from 0.8 to 1.5 centimeters. End portions can typically have a uniform or substantially uniform width along the length, normally not varying by more than about 25 percent of the average width along the length of the installed portion of the end portion.

According to exemplary implants, a central support portion can have a width that is greater than a width of an end portion, e.g., the width of the end portion at a location that is adjacent to a load-transfer portion. A central support portion that has a width that is greater than a width of the end portions can improve contact between the implant and tissue to be supported by the implant. An increased width of a central support portion may take the form of one or two lateral extensions or "lobes" that extend laterally in at least one direction (an anterior direction) for contacting tissue being supported. An anterior extension supports tissue that is relatively anterior to a patient's anatomy compared to an otherwise similar central support portion that exhibits a smaller width. Alternately, a central support portion may include two lateral extensions in each of an anterior lateral direction and a posterior lateral direction, to contact tissue both anterior and posterior to a central support portion of a relatively more narrow width.

An increased width, e.g., in an anterior direction, can provide for increased contact and frictional engagement between a central support portion and pelvic tissue such as a urethra, tissue that supports the urethra, bladder neck, bulbous spongiosum, vaginal tissue, etc., being supported. A widened central support portion provides a larger area of contact between the implant and a pelvic tissue and can have a reduced tendency to fold or deform upon tensioning of the sling. Increased contact area between a central support portion and pelvic tissue can further allow for improved ability to re-locate or approximate tissue if desired during implantation of the sling and treatment and support of pelvic tissue by use of the sling. A widened central support portion also may reduce the amount of pressure (force) exerted onto tissue, per area of supported tissue, which may reduce risk of tissue necrosis or erosion.

Adjacent to a central support portion, and connecting the central support portion to one or preferably to both end portions, can be one or two load-transfer portions. The load-transfer portion exhibits a width that is greater than a width of an end portion, such as the width of the end portion at the location at which the end portion connects to the load-transfer portion. The load-transfer portion also includes a width that is less than the width of the central support portion. Functionally, the load-transfer portion allows a load placed across the central support portion, between the end portions, to be distributed across a width of the central support portion that is greater than widths of the end portions.

The dimensions of load-transfer portions can be sufficient to allow for overall functional capabilities of an implant. Exemplary dimensions of a load-transfer portion may include a length extending between an end portion and a central support portion of from about 0.2 to about 2 centimeter, such as from about 0.3 to about 0.7 centimeters. The width of a load transfer portion normally varies between the width of the central support portion (where the load-transfer portion connects to the central support portion), and the width of the end portion (where the load-transfer portion connects to the end portion). The width can increase gradually along the length between the end portion and the central support portion, either in a straight line, a curved or arcuate line, or otherwise, as desired.

A urethral sling may preferably include two load-transfer portions, one connecting each end portion to the central support portion. A load-transfer portion may extend laterally in an anterior direction toward a central support portion that is widened in an anterior direction. Alternately a load-transfer portion may extend bi-laterally in an anterior direction and in a posterior direction, toward a central support portion that is widened bilaterally in both anterior and posterior directions.

A load-transfer portion may extend between an end portion and a central support portion by a path along an edge that results in a width of a load transfer portion that gradually changes from the width of the end portion to the width of the central support portion. This changing width may define a path, along the edge of the load-transfer portion, that is straight, arcuate, or a combination of straight and arcuate, and that functionally allows a load placed across the central support portion, between the end portions, to be distributed across a width of the central support portion that is greater than widths of the end portions. An advantage of a load-transfer portion as described is that the width of the load-transfer portion, being greater than the width of an end portion, allows for a force applied across the central support portion to be spread out across a greater width of the central support portion (compared to an implant that does not include a load-transfer portion as described herein). Spreading the force to a width that is at least greater than the width of the end portions can reduce or prevent deformation of the central support portion upon placing a force across the central support portion. Deformation can be in the form of "curling" of the central support portion when a load is placed in opposite directions along the end portions.

Exemplary implants include end portions that include side edges ("edges") and edge extensions. The edge extensions exist due to the porous or "open pore" nature of the material used to prepare the end portion. The edge extensions can be reinforced to cause the end portion to resist movement within tissue, during implantation, after implantation, or both. Reinforced edge extensions provide increased frictional resistance of an end portion from movement within the tissue, which provides desired short-term fixation properties of end portions within tissue during and immediately after installation, i.e., the ability of the end portions to stick and hold into flesh when installed without moving and potentially without stretching.

Edge extensions can be reinforced by any mode, such as by reinforcing open pore material adjacent to the edge (e.g., without necessarily treating the edge itself) in a way that limits movement of edge extensions and produces a stiffened edge extension. Other reinforcement can be in the form of a stiffening or reinforcing coating applied directly to edge extensions, optionally also adjacent to edge extensions, to limit the movement of the edge extensions. Reinforcement may also include combinations of treatments or features of edges or of areas of porous material adjacent to edges. Thus, a reinforcement may include or contact an edge (i.e., an end of an edge extension), may be adjacent to an edge but not include the edge (end of edge extension) itself, may contact an edge and an area adjacent the edge, or may contact some portions along an edge of an open pore material and not other portions along the same edge while also including or contacting area adjacent to the edge. With any of these reinforcements, the force required to pull a reinforced elongate strip through tissue can be increased.

Without limitation, any useful dimensions between edge extensions, edges, and reinforcement of an extension portion or implant can be used in association with the invention. Reinforcement can be placed at any useful distance from an edge, up to and optionally including the material at an edge. As exemplary values, an extension portion can have a length (measured laterally from the end portion as a distance perpendicular from longitudinal axis of an extension portion) in the range from 0.02 to 0.3 inches, e.g., from 0.05 to 0.1 inches.

Reinforcement located adjacent to an edge and not contacting the edge may be located a distance sufficiently close to the edge extensions to produce stiffening of the edge extensions. Typically this location may be at or near a first junction relative to an edge or at a first solid area relative to an edge. In terms of distance, a useful distance from an edge may be in the range from 0.02 to 0.3 inches, e.g., from 0.05 to 0.1 inches, which can coincide with a first junction or a first solid area of an end portion material.

A reinforcement adjacent to an edge may be in the form of any type of material, method, or technique that will improve the strength or stiffness of edge extensions to increase the force required to pass the end portion through tissue. By way of example, a reinforcement may include a material added to or formed or incorporated into an open pore material at a location adjacent to an edge, and optionally not contacting the edge (the end of an edge extension). A reinforcing material may be polymeric or non-polymeric, and may be the same as or different from the material of the open pore material itself. A polymeric material could be a length of interrupted or continuous adhesive, plastic, or thermoplastic materials, or any other polymeric or non-polymeric material that can be incorporated into the open pore material at the described location to stiffen and reinforce an edge extension. A reinforcement adjacent to an edge may alternately or additionally be in the form of a stiffening weave or knot adjacent to an edge, such as a reinforcing weave or knot at a first junction, that is different from knots or weaves at other positions of an end portion.

An exemplary reinforcement may be a strip of continuous or discontinuous solid material such as a stiffening strand that is applied to or that is embedded, formed, or woven, or otherwise incorporated, into an open pore material at a location adjacent to an edge along a length of an end portion. A stiffening strand could be a continuous straight piece of material that is applied by an adhesive, that is molded into a film, or that is woven into a mesh, etc. Examples of suitable stiffening strands could include strands of plastics, bioresorbable materials, thermoplastics, natural materials such as yarns or threads, etc., that are incorporated into an end portion adjacent to an edge.

Another example of a reinforcement adjacent to a strip edge could be a weave of a mesh that includes different weaving or knots at a junction or knot adjacent to the edge, e.g., at a first or second junction relative to an edge.

Still another example of a reinforcement adjacent to an edge of an end portion of an implant is a heat processed area of film or mesh such as a continuous or semi-continuous area of heat-treated film or mesh. Heat treatment may melt a polymeric (e.g., thermoplastic) film, strand, or mesh, to cause the film, strand, or mesh, and any adjacent edge extension, to be strengthened and resist movement, such as at a melted junction or knot of a woven mesh. Exemplary heat treatment may be used to heat treat area of an end portion adjacent to an edge, including one or more of a first junction, a second junction, a strand or solid portion of an open pore material between the first and second junction, a portion of an edge extension, or any other area of an end portion adjacent to an edge.

Other examples of urethral slings are described in Assignee's copending U.S. patent application Ser. No. 11/346,750, entitled "Transobturator Surgical Articles and Methods," filed on even date herewith, the entirety of which is incorporated herein by reference. That application describes slings that include a widened central support portion to provide increased area of contact between the central support portion of the sling and the tissue being supported, preferably and optionally in combination with a load transfer portion between end portions and the central support portion.

Figure 9A:
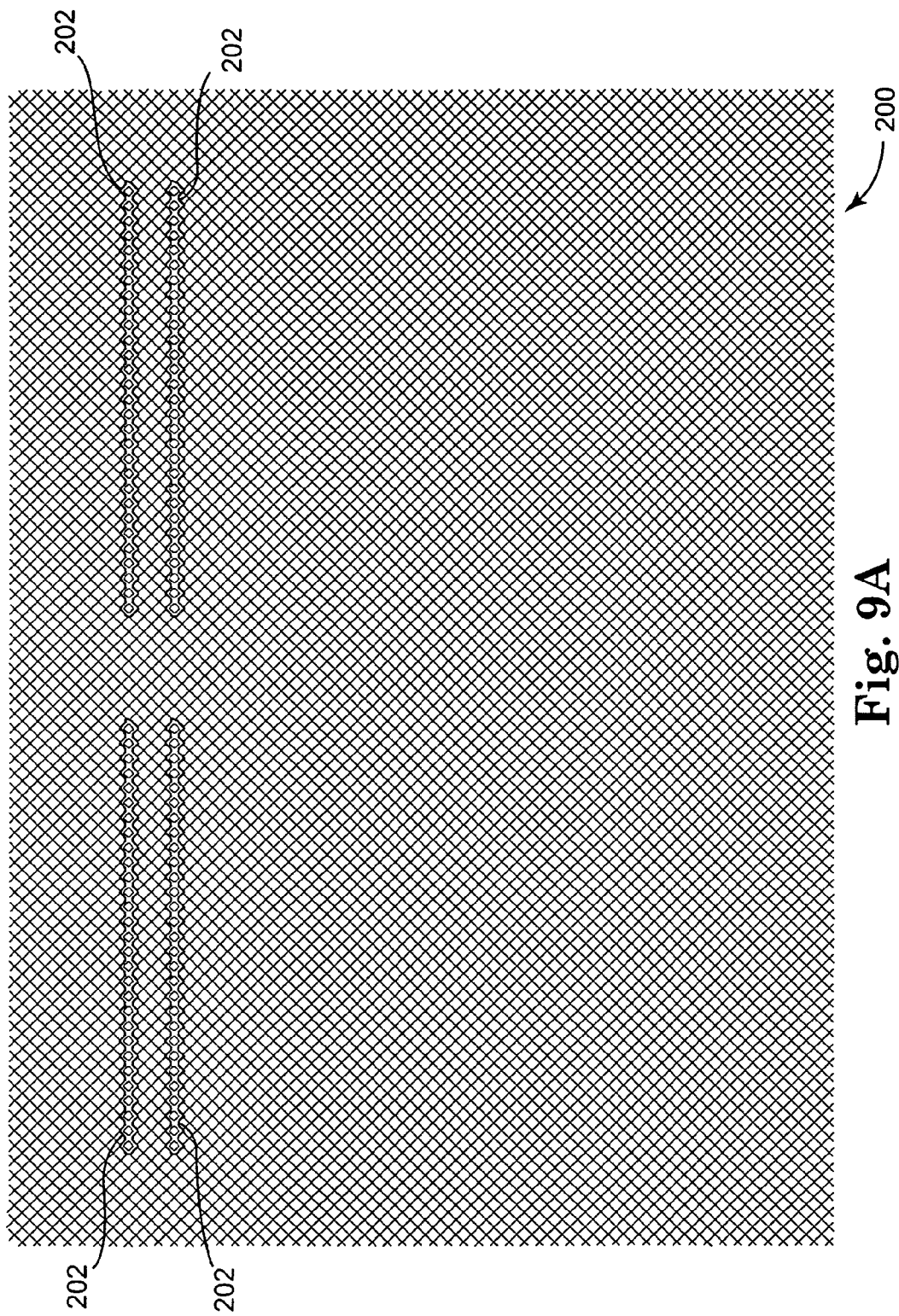
FIGS. 9A, 9B, and 9C, illustrate a porous material and an exemplary urethral sling prepared from the porous material.
Figure 9B:
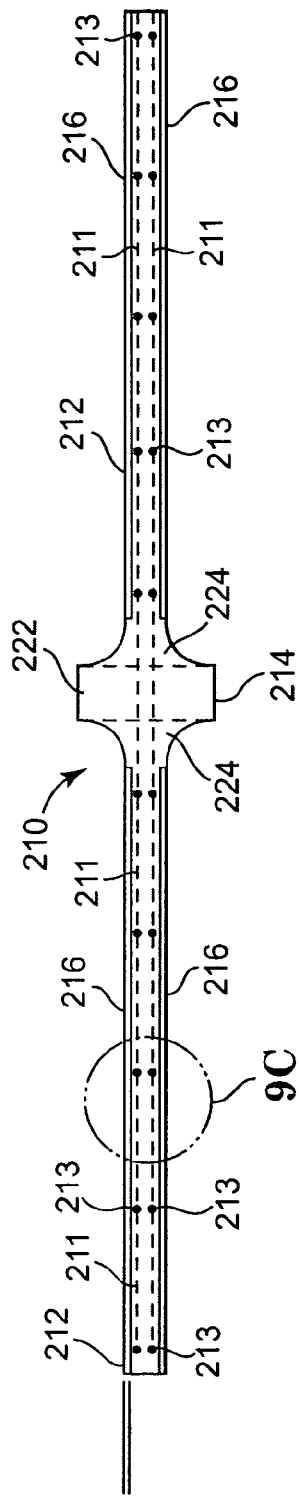
Figure 9C:
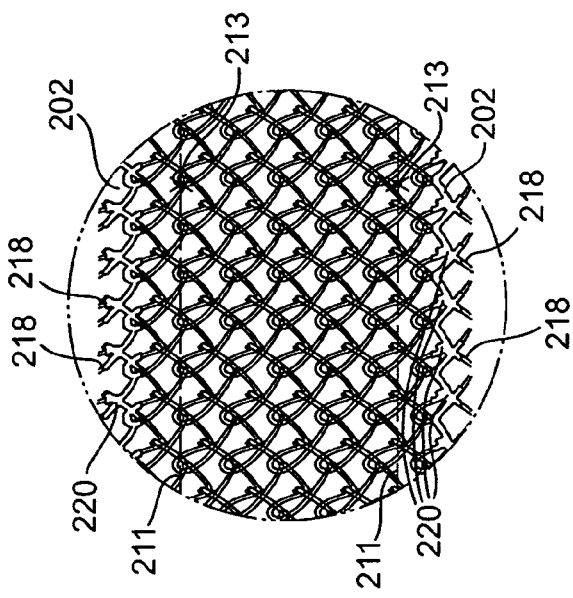

An example of a useful method for preparing an implant having reinforced edge extensions based on heat-treatment is illustrated at FIGS. 9A, 9B, and 9C. FIG. 9A shows a sheet of open pore material 200, which is illustrated as a woven mesh but which may be any open pore material. Mesh sheet 200 is sized substantially larger than the total dimensions of a mesh implant that will be formed from sheet 200.

FIG. 9A illustrates treated (e.g., heat-treated, coated, etc.) open pore material 202. Treated material areas 202 can be in the form of lengths of heat-treated open pore material (e.g., mesh) extending along a desired path of open pore material. As an example, heat-treated open pore material 202 may uniformly contact a longitudinal area that includes a series of adjacent pores along a length of mesh 200. Alternately or in addition, heat-treated material 202 may uniformly contact a longitudinal area that includes a series of adjacent junctions of mesh strands (e.g., knots) or other junctions or intersections of mesh 200. Contacting either a series of adjacent pores or junctions of a porous material can result in a uniform pattern of heat-treated material, e.g., a uniform length-wise area of heat-treated junctions, a uniform length-wise of heat-treated pores, or an area that includes pores and junctions.

In one specific embodiment a heat-treated material 202 includes heat-treated junctions (e.g., knots or weaves) of a mesh material. With a location of heat treatment that includes a heat-treated junction of a mesh, cutting the mesh can be performed along a line that includes open pores that are immediately adjacent to and substantially parallel to the area that includes the series of heat-treated junctions. Upon such cutting step, edge extensions of non-heat-treated severed mesh strands result adjacent to elongate areas of heat-treated mesh junctions.

FIG. 9B illustrates an embodiment of a urethral sling cut from mesh 200 after formation of heat-treated material 202. Urethral sling 210 includes two extension portions 212 extending from central support portion 214. Sutures 211 extend along the length of implant 210, attached at multiple attachment points 213, which may include adhesive, knots, thermally bonded mesh material, etc. Urethral sling 210 includes a widened central support portion and two load-transfer portions, one on each side of the central support portion. The load-transfer portions are "bi-arcuate" load transfer portions, meaning that each of the two load transfer portions includes two arcuate edges one extending in posterior and one extending in an anterior direction.

Extension portions 212 include edges 216 extending at the location of a cut made in mesh 200, following heat-treatment to form heat-treated material 202. Each of edges 216 includes edge extensions 218 and reinforcement in the form of heat-treated material 202. FIG. 9C illustrates a close-up of edges 516, including mesh of extension portion 212, edge extensions 218 in the form of severed strand of un-heat-treated material, and heat-treated material 202 that includes a first row of fiber junctions (e.g., knots) 220 adjacent to edge extensions 218.

Still referring to FIG. 9C, the distance of the reinforcement of edge extensions 218, i.e., heat-treated material 202, from edge 216, can be any distance that stiffens edge extensions 218, and may depend on factors such as the type of mesh, size of connecting strands of mesh, size of knots, and length of edge extensions. For purposes of illustration, the two lengthwise strips 202 located along each edge 516 may be at least 0.05 centimeter (measured laterally, perpendicular to the length of the edge) from the severed ends of edge extensions 518, e.g., from 0.1 centimeter from the severed ends of edge extensions 518.

A surgical implant such as a sling can be implanted using a needle as described, without the need for bone screws. The precise, final location of the sling will depend on a variety of factors including the particular surgical procedure(s) performed, and any preconditions of the patient such as scar tissue or previous surgeries. For example, it may be preferred to place the sling in close proximity to, but not in contact with, a mid portion of the urethra to treat incontinence. Alternatively, the sling may be placed near the bladder neck or near the bulbous spongiosum (BC).

Tools of the invention can be used for transobturator methods in male and female anatomies, e.g., to implant a urethral sling ("sling") to treat urinary incontinence. "Transobturator" methods generally involve two lateral incisions at the left and right inner thigh regions, each near a patient's obturator foramen, and a third, medial external incision at the perineum. The sling is installed between the medial incision and the two lateral incisions with a central support portion of the sling being placed below the urethra, to support the urethra, not necessarily in contact with the urethra itself but optionally and preferably in contact with tissue below the urethra. The sling can be then tensioned to approximate pelvic tissue to improve continence. Transobturator methods are described in Assignee's copending U.S. patent application Ser. No. 11/347,047, entitled "Transobturator Methods for Installing Sling to Treat Incontinence, and Related Device," filed on even date herewith; the entirety of which is incorporated herein by reference.

According to U.S. Ser. No. 11/347,047, titled Transobturator Methods for Installing Sling to Treat Incontinence, and Related Device, filed on even date herewith, a patient may suffer from pelvic tissue prolapse, weakness, or dislocation, due to one or more factors of age, weak and sagging perineal floor muscles, as a result of a surgical procedure to the prostate such as a partial or radical prostatectomy, or for any other reason. Pelvic tissue prolapse may be in the form of mispositioning of one or more component pelvic tissue that makes up the urinary sphincter complex. A urethral sling can be installed to approximate and support pelvic tissue, e.g., of the urethra, perineal body, urethral sphincter complex, etc., in any way that improves positioning of pelvic tissue to improve coaptation of the urethra, resulting in improved continence. According to one embodiment described therein, a central support portion of a sling may be placed below the bulbospongiosus muscle and tensioned to re-position pelvic tissue and improve continence. In particular embodiments for treating male incontinence, a urethral sling can be installed using a tool as described herein, and a transobturator tissue path, by placing a central support portion of a sling in direct contact with the corpus spongiosum.

In other embodiments of a transobturator method, a single needle may be useful to place left and right end portions both left and right sides of a patient. A single left-handed needle (alternately a single right-handed needle) can be used to place a right side of the sling on a patient's right side, using a transobturator tissue path between a perineal incision and a patient's right-side lateral incision. In the same procedure, the same left-handed needle may also be used to place the opposite end portion on the patient's left side. While the left-handed needle is not optimal for placement at the patient's left side, it can be effective. Systems or kits of the invention can include a single left- or right-handed needle with an implant, for surgical implant according to this method.

The invention also includes surgical kits, assemblies, and systems that include at least one tool, optionally two tools, as described herein. In a preferred embodiment, a kit comprises at least on surgical instrument such as one of those shown in any of FIGS. 1-6, and a urethral sling such as a polypropylene sling mesh assembly with attached dilators. Such a kit may be provided for the placement of a sling for the treatment of male and female stress urinary incontinence (SUI) resulting from urethral hypermobility and/or intrinsic sphincter deficiency. Exemplary kits may include a tool arranged to provide an ergonomic advantage as described and a urethral sling. In a kit for the male anatomy (or a larger female anatomy) a tool may be sized or shaped with larger dimensions such as a larger width or length of a three-dimensional portion; the sling may be designed for use in the male anatomy with increased strength and short and long-term fixation properties. The sling may be designed, for example, for placement below the CS, may include a widened central support portion, load transfer portions, reinforced edge extensions, multiple sutures, sutures attached at multiple attachment points, etc.

The various embodiments of three-dimensional needles described above preferably include a substantially straight spacer portion emerging from an end of the handle portion preferably along the handle axis. This helps afford convenient passage of the needle using an ergonomic wrist roll adopted by some surgeons. The three dimensional needles also include a structure that can be described as a variable spiral portion extending from the distal end of the straight spacer portion. As shown, the spiral portion is preferably variable as the angle of the spiral portion changes between the end of the extension portion and the distal end of the needle. The shape of the spiral portions help avoid over insertion of the needle into the body which helps avoid damage to the sensitive structures in this region of the body.

All patents, patent applications, and publications cited herein are hereby incorporated by reference in their entirety as if individually incorporated.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

EXAMPLES OF SURGICAL PROCEDURES

Example 1

Several methods are contemplated herein. Although the methods of use as disclosed herein generally relate to female incontinence conditions and treatments/procedures, male incontinence conditions and treatments/procedures are also included within the scope of the present invention. Further, the term "urethra," with respect to sling positioning, is used for brevity and reader convenience. It should be noted that the present invention is particularly suitable for placing a sling in a therapeutically effective position. The method may be used to support a variety of structures at different anatomical locations. Variations of these methods may occur due to individual surgeon's techniques or a patient's particular anatomy.

The present invention uses an obturator passage of the needle, preferably in a direction from the anterior to the posterior side of the pubic bone. An obturator approach affords a sling procedure where previous scarring in the region of the retropubic space or other anatomical features would prevent or restrict a traditional pubomedial sling procedure. An obturator approach is also likely to avoid bladder perforations, a possible but rare complication with some prior art pubomedial procedures. It may also be more convenient to conduct a concomitant repair (e.g. cystocele repair) with a sling inserted with a side approach as the sling is placed in a more horizontal position than the U-shaped sling procedures of the prior art.

Initially, the patient is placed under local, spinal, or general anesthesia. A small transverse or medial incision is made in the anterior medial wall of a patient followed by a transurethral dissection. The amount of dissection may vary according to surgeon preference. Preferably, dissection is sufficient to allow the surgeon's finger to meet the end of the three-dimensional region of a needle as described herein, after the needle passes through the obturator foramen.

Two small incisions are also made near the obturator foramen to afford needle entry. Notably, the precise location of the stab incisions may vary according to surgeon preference. For example, some surgeons may place the incision adjacent the obturator opening of the pubic bone. Other surgeons may slightly offset the incision in order to use the bias provided by the patient's tissue to urge the tip of the needle in a direction toward the posterior surface of the pubic bone.

The surgeon's finger is initially placed in the medial incision sufficient to meet the end of region of the needle after it passes through the obturator foramen. A path for the needle through the obturator foramen that is substantially free of vascular and nerve passages is selected. To select the path, the surgeon preferably initially identifies the anatomical structures of the pelvis such as the ischial tuberosity and obturator foramen by palpation of the tissue.

In one example embodiment, the surgeon seeks to use the posterior portion of the patient's pubic bone as an anatomical guide to controllably move the tip of region of the needle toward the medial incision and to help avoid damaging structures. The surgeon exploits the tactile feel provided by the posterior portion of the pubic bone to controllably pass the tip of the needle. This approach is preferred as it helps keep the needle away from the bladder and other vulnerable tissues.

The sling is placed in a therapeutically effective position. Other positions are contemplated herein. The precise anatomical position will depend upon a variety of factors including the type and degree of anatomical damage or insufficiency, location of significant scar tissue, whether the sling procedure is combined with other procedures and other surgeon decisions. The sling can be placed in one of various useful positions to treat a pelvic condition, such as to support the bulbous spongiosum (BC), the urethra (directly), or another tissue to support the floor of the pelvis.

Example 2

Exemplary Male Transobturator Sling System and Method

An exemplary sling system consists of two single-use surgical instruments called "needle passers" ("tool" or "needle") and a mesh implant with attached connectors, provided sterile. One end of each needle passer is keyed to allow for secure placement of the dilating connectors. Each needle passer has a plastic handle attached. The mesh is constructed of polypropylene monofilament that is precut to 1.2 centimeters arm width, 3.55 centimeters center width, and 35.5 centimeters length. Two absorbable tensioning sutures are threaded into the length of the sling system mesh to allow for tensioning adjustment of the sling system mesh after placement in the patient. Two plastic sheaths are placed over each arm of the sling system mesh to aid in ease of placement. The dilating connectors are attached to the ends of the needle passers during the procedure. The mesh is intended to remain in the body as a permanent implant and the mesh component is not absorbed or degraded by the action of tissue in-growth or tissue enzymes.

The system is intended for the placement of a pubourethral sling system for the treatment of male stress urinary incontinence (SUI) or intrinsic sphincter deficiency (ISD).

The procedure can be carried out under local, regional or general anesthesia. A small vertical incision is made in the area of the perineum followed by periurethral dissection. Two small stab incisions are also made above the obturator foramen for needle entry.

Preparation

1. Patient should be placed in a dorsal lithotomy position.
2. Genital area should be shaved.
3. After shaving, the area should be scrubbed with Povidone-iodine soap for ten minutes or the approved hospital pre-operative scrub procedure.
4. Ensure that the bladder is empty. A Foley catheter is not required but may aid in identifying the urethra during the procedure.

Dissection

1. The scrotum is elevated and a perineal incision is made, beginning midline at the level of the inferior edge of the symphasis and running approximately three centimeters toward the rectum.
2. The incision is carried deeper through Colles' fascia. The urethra is then mobilized by separating the bulbocavernosus muscle from the central tendon of the perineum.
3. The bulbocavernosus muscle is separated at the midline raphe and carefully dissected away from the corpus spongiosum.
4. A finger is placed between the bulbocavernosus muscle and the corpus spongiosum and with blunt dissection, the intersection of the corpus spongiosum and the perineal membrane is found.
5. The needle is inserted into the obturator foramen at a point bordering the inferior pubic ramus defining the foramen which lies approximately one-third of the distance below the forminal apex. Palpate the inferior pubic ramus and feel for the bony landmarks to locate the proper position. A needle through the skin can be used to probe the bone to help confirm that the correct location for the needle passer entry point is found, but it is not required. The position of entry is just below the medial aspect of the palpable part of the adductor longus tendon. The ideal position is at a point at the inner and medial aspect of the obturator foramen as high as possible to the foraminal apex.
6. Make small stab incisions at the correct location over both obturators (obturator foramina). Confirm that both marks lie in a straight line at the level shown in FIG. 6.
7. The patient is now ready for needle passage.

Passing the Insertion Needle Through the Obturator Foramen

1. Identify needle designated for the patient's left side.
2. Point the needle tip perpendicular to the skin and insert the needle into the patient's left stab incision previously made over the obturator foramen. The goal is to start with the needle tip hugging the medial aspect of the inferior pubic ramus within the obturator foramen at the level of the point one third below the cephalad peak of the obturator foramen.
3. Insert the needle to the level of the obturator fascia while hugging the bone with the needle tip.
4. Place an index finger in the perineal incision between the intersection of the corpus spongiosum and the perineal membrane on the side of the corpus spongiosum closest to the needle entry point.
5. When passing the needle on the patient's left side, keep the surgeon's right hand on the needle handle and left index finger in the perineal incision. The surgeon's left thumb should be on outside curve of needle to control the needle movement.

Figure 11:
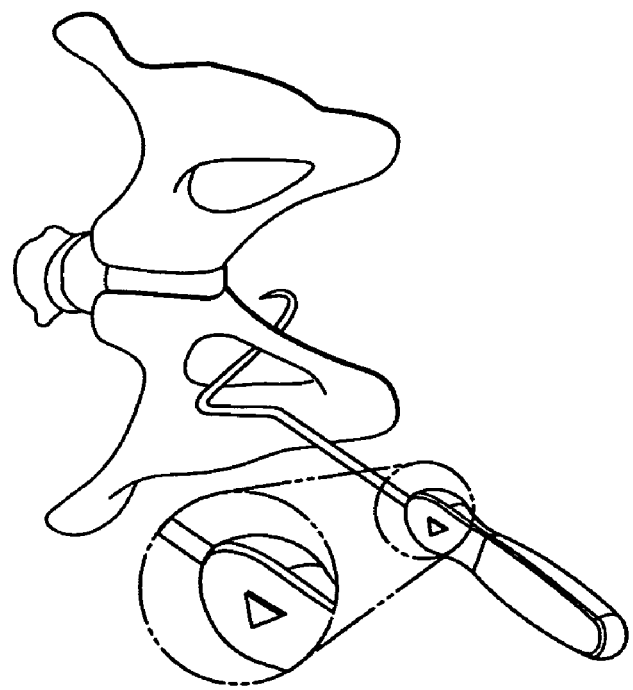
FIG. 11 illustrates an exemplary step of a surgical procedure as described.
Figure 10:
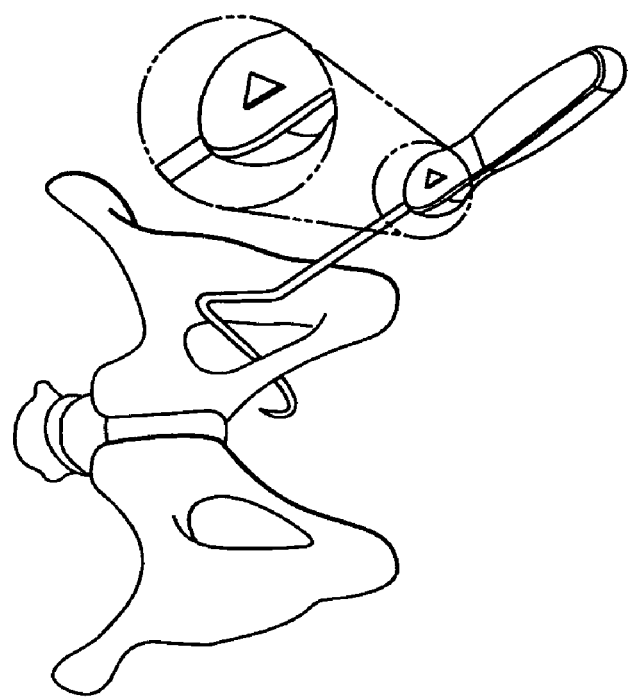
FIG. 10 illustrates an exemplary step of a surgical procedure as described.

See FIGS. 10 and 11.

6. Using the left thumb on the outside curve of the needle for to control needle movement, push the needle through the muscles and obturator fascia by turning the needle handle clockwise using the right hand. The needle tip penetrates until resistance of the tissue stops—about 0.5 centimeters.
7. Immediately locate the ischial pubic ramus with the needle tip and rotate the needle handle to allow the needle to follow the posterior ischial pubic ramus surface.
8. The index finger tip must palpate the needle tip while the needle is under the perineal membrane. The goal is to have the needle tip pass through the perineal membrane medial to the ischiocavernosus muscle, lateral to the corpus spongiosum and just below the level where the urethra passes through the perineal membrane. If not, move the needle to meet the finger tip. If the needle tip cannot be located, then the needle must be withdrawn just behind the ischial pubic ramus and carefully advanced again.
9. When the needle tip is in the correct position, guide the needle tip using the index finger through the perineal membrane until the needle extends through the incision.
10. Repeat the needle passage procedure (steps 2-9) on the patient's right side, with the needle designed for the right side.

Placing the Sling System Mesh

1. Attach connector from the implant to needle end. One connector should be attached to each of the needles on the end protruding from the perineal incision. Orient the knots of the tensioning sutures to be facing outward, away from the urethra. Be sure that the sling system mesh lies flat and that the mesh is not twisted prior to attaching each connector.
2. Once both ends are connected, retract one needle along the same pathway, guiding with the fingertip.
3. Cut the insertion sheath and mesh at the external end of the plastic sheath and discard the needle, attached connector, sheath end, and mesh end. This step allows the sheath to slide freely relative to the mesh. Leave enough sheath material above the level of the skin so that the sheath can later be removed.

4. Repeat for the other needle on patient's contra lateral side to loosely position the sling system with the tensioning sutures facing outward, away from the urethra. Loosely position the sling system with the center of the central portion of the mesh sling approximately 1 centimeter distal to the line created between the needle passages on both sides of the corpus spongiosum.

5. In an optional step, before tensioning the sling, use two tack sutures to secure the placement of the sling to the midline of the corpus spongiosum. The sutures should be placed through the distal "flap" (anterior extension of the central support portion of the sling) just off of the center of the sling (at least two pores in from the edge of the sling mesh) and pass shallowly through the midline of the corpus spongiosum. When the sling is tensioned it will reposition the posterior urethral bulb approximately 14 centimeters proximal while elevating the perineal membrane.

6. The traction is parallel to the posterior urethra, which repositions the urethral lumen, rather than obstructing it.

Adjusting the Sling System Tension

1. If tissue retraction has been used, it must be removed before adjusting the tension of the sling system. If a Foley catheter has been used, it must also be removed before adjusting the tension.

2. The mesh is properly tensioned by simultaneously pulling on the ends of the sling system mesh and noticing approximately 14 centimeters proximal movement of the urethra.

3. If the patient is under spinal or regional anesthesia, the position of the sling can be verified by a cough test after filling the bladder, at the discretion of the surgeon.

To Loosen the Sling System Mesh:

Place an instrument between the sling system mesh and the urethra. Ensure that both the mesh and the tensioning sutures are located beneath the clamp. Use the clamp to pull down and loosen the sling system mesh as desired.

To Tighten the Sling System Mesh:

Clamp a device such as a hemostat, across the sling system mesh, at the lateral incisions. Be sure that both the tensioning sutures and the complete width of the sling system are captured within the clamp. The sling system mesh may be rolled around the clamp to improve the grip. Pull up to tighten the sling system mesh as desired. If needed, this can be repeated on the contra lateral side.

Remove the plastic sheath from the sling system mesh and discard. Confirm the correct tension of the sling system after the sheath has been removed.

Trim the sling system mesh at the level of the subcutaneous tissue.

Complete a multi-layer closure of the perineal incision and the skin incisions.

Immediate Post-Operative Care

A catheter can be used at the discretion of the surgeon.

Antibiotic prophylaxis should be given.

The ability of the patient to empty the bladder should be confirmed.

Example of Method of Preparation of Urethral Sling with Widened Central Support Portion and Reinforced Edge Extensions Exemplary urethral sling implants according to the invention were prepared according to the following, by the steps, in order, of (1) providing a sheet of mesh material, (2) heat treating the mesh to produce a heat treated area, and (3) cutting the heat treated mesh to form a urethral sling that includes reinforced edge extensions on end portions.

Step 1—Heat Treating or "Sealing" Mesh

A sheet of polypropylene knitted mesh was provided for treatment in a heat-treatment or heat-sealing machine. The mesh was of the type used in the MONARC™ and SPARC® female urethral slings used for treating female urinary incontinence, from American Medical Systems, Inc., of Minnetonka Minn. The mesh is that type that includes a "smooth" side and a "rough" side, as is known. The rough side may have a very slightly more rough feel compared to the smooth side; with reference to the direction of the loop that forms the weave, the loop points slightly more toward the "rough" side surface and slightly away from the "smooth" side surface. The "rough side" may be referred to as the "Technical Face" or "Loop Side" and the "smooth side" is called the "Technical Back" or "Lap Side". The invention can preferably apply heat ("sealing") at the Technical Back side of this type of mesh.

The pores are diamonds that have a size including an approximately 0.060" diameter measured (corner to corner) at the longer dimension and a 0.050" diameter measured in the shorter "width" direction (corner to corner). The sheet has rows of alternating diamonds that face up (the smallest angle point of the diamond faces up) adjacent to diamonds that face down (the smallest angle point of the diamond faces down).

The machine was turned on and set machine to the following cycle parameters:

| | |
|---|---|
| Temp of heated sealing element: | 395° F. (±5° F.) |
| Pressure applied to mesh by sealing element | 35 psi (±5 psi) |
| Time of pressure application | 0.9 sec (±.1 sec) |

Figure 13:
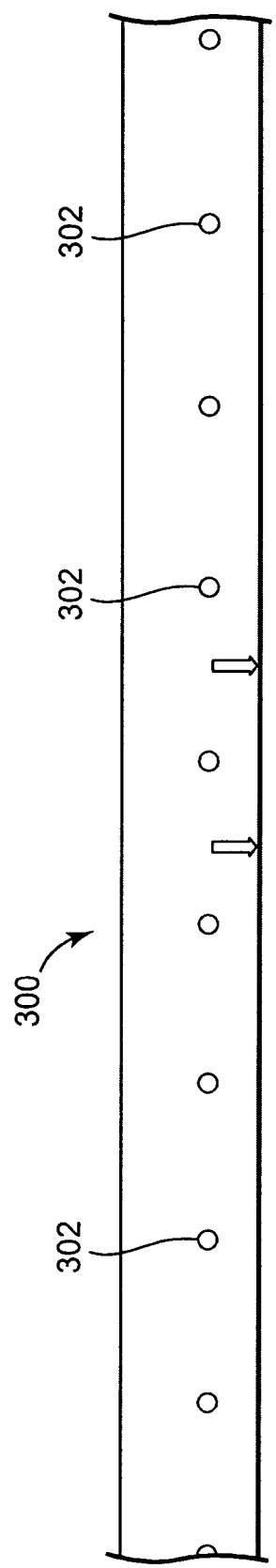
FIG. 13 illustrates exemplary equipment useful for preparing an implant.

The mesh was loaded rough-side-down onto a plate insert that includes a line of several pins that are inserted into the pores of the mesh. The plate insert fits into a groove for positioning the plate and mesh below a heat treating element and a cutting die, for heat treating and cutting at locations of the mesh to produce heat treated reinforcement adjacent to edges, i.e., reinforced edge extensions. A portion of a plate is shown at FIG. 13, which shows plate 300 and pins 302 (not to scale). Pins 302 are not at the center of the width of the plate but are located closer to one side (referred to as the "short side," and indicated with the arrow) than the other side. This is because of the asymmetry of the "diamond"-shaped pores used to prepare the urethral sling of the present example. The offset of the pins allows a cut of the mesh to align with pore openings as desired, and also allows heat sealing to align as desired, e.g., at a first junction of the mesh.

Figure 14:
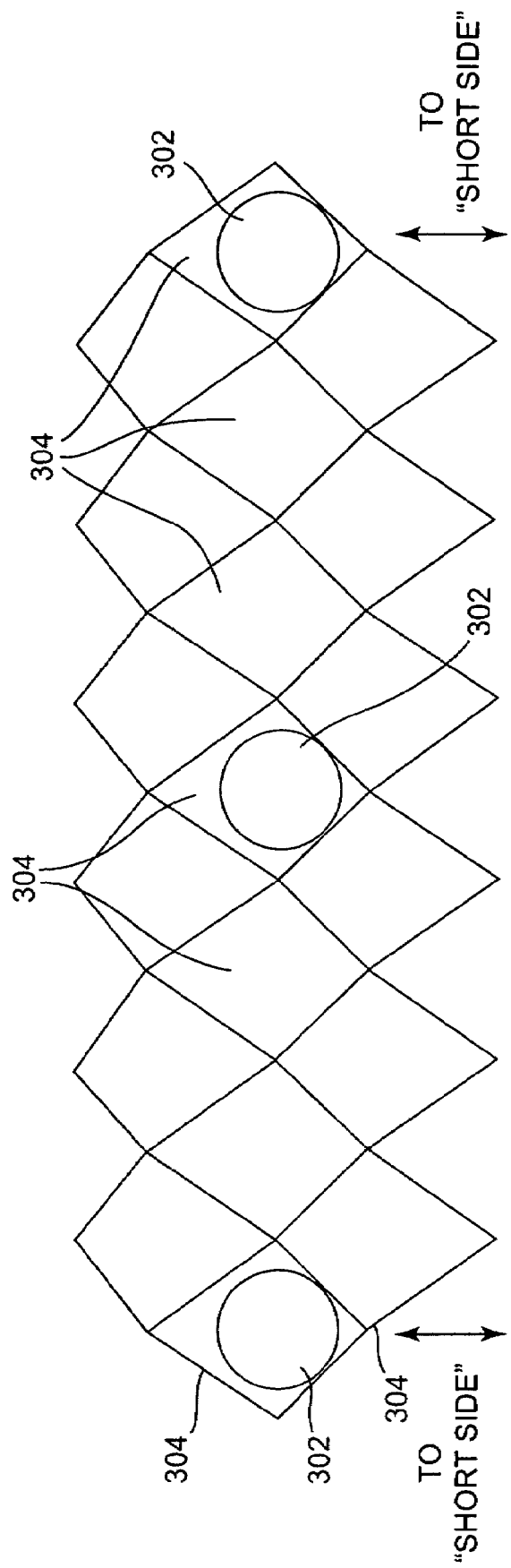
FIG. 14 illustrates an exemplary processing step of preparing an implant.

The mesh is aligned such that the pins of the plate are placed in the same row of pores of a mesh, with the pores being aligned along the length of the end portion as diamond-shapes as opposed to square-shapes (see FIG. 14). More specifically, because the diamonds of are asymmetrical, the diamonds are aligned with an orientation that points the smaller angle of the diamond in a direction away from the "short side" of the plate (indicated by arrows), i.e., the "diamond facing up" pores are held by pins 302. See FIG. 14, which schematically illustrates that pins 302 located to hold a single "row" of upward-facing diamonds 304, of with all diamonds held by pins 302 facing in the same direction.

A "mesh hold-down" piece is used to hold the mesh against the plate. The hold-down is made of Teflon and fits over the mesh and pins of the plate and does not otherwise interfere with the heating element contacting the mesh.

Load the mesh and plate into the heat seal machine, making sure the mesh is laying flat. Initiate heat treatment cycle with the parameters identified above.

Remove Mesh Hold-Down.

Step 2—Die Cutting the Sling

Figure 12:
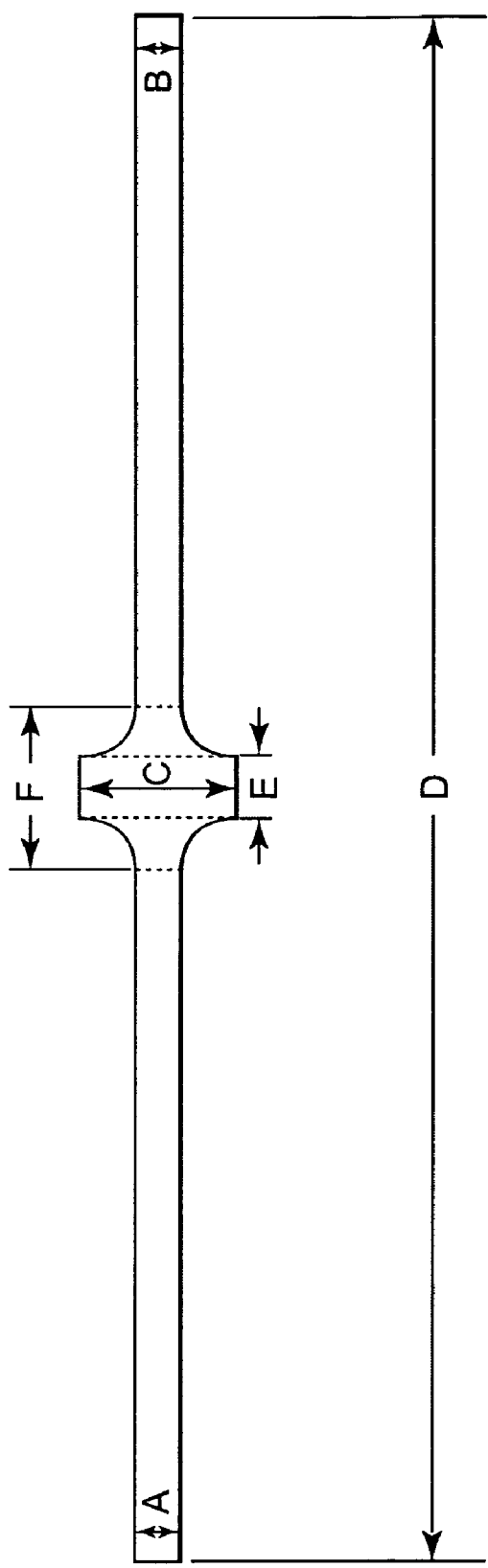
FIG. 12 illustrates exemplary equipment useful for preparing an implant.

A pneumatic press, cutting die, plate insert, and attached mesh (above) are provided. The die includes a blade that is shaped like a one-piece urethral sling, with the following dimensions, as shown in FIG. 12.

| Dimension | Measured Value |
|---|---|
| A | 0.44" |
| B | 0.44" |
| C | 1.4" |
| D | 14" |
| E | 0.58" |
| F | 1.5" |

The pneumatic press is set to 55 psi (±5 psi).

The plate with the mesh on it is placed into the cutting die. This lines up the cut to be adjacent to the heat-treaded portion of the mesh.

The die and mesh are placed in to the pneumatic press and the stamping cover with the plastic side down is placed on to the die.

The press is activated to cut out the sling.

If any strands of the sling did not cut, a pair of scissors can be used to separate the sling from the mesh panel along the cutting line of the die.

If necessary, edges of the sling may be cleaned with a bristled brush to remove any loose sling material.

The invention claimed is:

1. A surgical instrument for implanting an implantable material to a pelvic region, the instrument comprising:
   a handle having a longitudinal axis and an elongate width dimension normal to the longitudinal axis, the elongate width dimension defining a midplane,
   a needle portion extending from the handle along the longitudinal axis, the needle portion comprising
      a spacer portion connected to the handle,
      a three-dimensional region connected to the spacer portion distal from the handle, and having structure in three dimensions, and
      a needle distal end at the distal end of the three-dimensional region,
   wherein the needle portion is sized and shaped to extend between an incision substantially adjacent to a patient's obturator foramen, through the obturator foramen, and to a medial incision; and
   wherein the needle distal end is located at an angle between 20 to 70 degrees from the midplane when viewed along the longitudinal axis, and
   wherein an angle between an axis of the needle end portion and the midplane, the angle being an acute angle defined by the needle tip, an intersection of the axis and midplane, and the longitudinal axis when viewed along the longitudinal axis, is in the range from 30 degrees to 60 degrees.

2. The instrument of claim 1, wherein the three-dimensional region defines a curved portion comprising a needle end portion, and an axis of the needle end portion lies in a plane orthogonal to the longitudinal axis of the tool.

3. The instrument of to claim 1, wherein the three-dimensional region comprises a portion shaped like a spiral, helix, or partial helix.

4. The instrument of claim 1, comprising a needle end portion at a terminal inch of the three-dimensional region that comprises a curve.

5. The instrument of claim 4, wherein an angle between the axis of the needle end portion, and a circle having an origin at the longitudinal axis and a radius defined by the needle distal end, when viewed along the longitudinal axis, is less than 15 degrees.

6. The instrument of claim 1, designed for use in a male transobturator sling installation procedure, wherein
   the needle portion is sized and shaped to extend between an incision substantially adjacent to a patient's obturator foramen, through the obturator foramen, and to a perineal incision,
   the three-dimensional region has a length in the range from 2.2 to 4 inches and a diameter in the range from 2.3 to 5 inches, and
   the three-dimensional region defines a helix that includes an axis of a needle end portion within a plane orthogonal to the longitudinal axis of the tool.

7. The instrument of claim 1 designed for use in a male transobturator sling installation procedure, by dissecting a transobturator tissue using an outside-in dissection technique.

8. The instrument of claim 1 in combination with a surgical implant for treating incontinence,
   wherein the implant comprises a central support portion and two elongate end portions, and
   wherein the needle end portion is adapted to be associated with an end portion of the implant.

9. The combination of claim 8, wherein the implant is a male urethral sling comprising one or more of a widened central support portion, reinforced edge extensions, or both.

10. A method of treating male incontinence comprising the steps of:
    creating a pair of lateral incisions substantially adjacent a patient's obturator foramen,
    creating a medial incision medial to the pair of lateral incisions,
    providing a surgical instrument according to claim 1, having a securement surface at the needle distal end,
    providing an implantable assembly adapted for treating the incontinence, the assembly having a surface complementary to the securement surface,
    passing the three-dimensional region having the securement surface between a lateral incision and the medial incision and through an obturator foramen,
    then associating the instrument at the securement surface with the implantable assembly to provide a removable attachment between the instrument and the assembly,
    then passing the implantable material through tissue from the medial incision toward a lateral incision.

11. The method of claim 10, wherein the three-dimensional region comprises a portion shaped like a spiral, helix, or partial helix.

12. The method of claim 10, wherein an angle between the axis of the needle end portion and circle having an origin at the longitudinal axis and a radius defined by the needle distal end, when viewed along the longitudinal axis, is less than 15 degrees.

13. The method of claim 10, wherein
    the three-dimensional region has a length in the range from 2.3 to 5 inches and a diameter in the range from 2.3 to 5 inches, and
    an axis of the needle end portion lies within a plane that is orthogonal to the longitudinal axis of the tool.

14. The instrument of claim 13, wherein a radial distance from a longitudinal axis of the spacer, to the needle distal end, is in the range from 0.7 to 1.4 inches.

15. The instrument of claim 1 wherein:
the three-dimensional region defines a curved portion comprising a needle end portion, and an axis of the needle end portion lies in a plane orthogonal to the longitudinal axis of the tool,
the three-dimensional region comprises a portion shaped like a spiral, helix, or partial helix,
a needle end portion at a terminal inch of the three-dimensional region comprises a curve, and
an angle between the axis of the needle end portion and a circle having an origin at the longitudinal axis and a radius defined by the needle distal end, when viewed along the longitudinal axis, is less than 15 degrees.

16. The method of claim 10, wherein
the needle distal end is located at an angle between 20 to 70 degrees from the midplane when viewed along the longitudinal axis, and
an angle between an axis of the needle end portion and the midplane, when viewed along the longitudinal axis, is in the range from 30 degrees to 60 degrees.

17. The method of claim 16, wherein a terminal inch of the needle end portion comprises a curve.

18. The method of claim 12, wherein
the needle distal end is located at an angle between 20 to 70 degrees from the midplane when viewed along the longitudinal axis, and
an angle between an axis of the needle end portion and the midplane, when viewed along the longitudinal axis, is in the range from 30 degrees to 60 degrees.

19. The method of claim 18, wherein a terminal inch of the needle end portion comprises a curve.

20. A surgical instrument for implanting an implantable material to treat incontinence, the instrument comprising:
a handle comprising a longitudinal axis,
needle extending from the handle, the needle comprising
a spacer portion connected to the handle, and
a three-dimensional region connected to the spacer portion distal from the handle, and having structure in three dimensions including a needle distal end at the distal end of the three-dimensional region, wherein
the needle portion is sized and shaped to extend between an incision substantially adjacent to a patient's obturator foramen, through the obturator foramen, and to a perineal incision;
the three-dimensional region has a length in the range from 2.3 to 5 inches and a diameter in the range from 2.3 to 5 inches, and
an axis of the needle end portion lies within a plane that is orthogonal to the longitudinal axis of the tools,
wherein an angle between an axis of the needle end portion and a tangent of a circle having an origin at the longitudinal axis and a radius extending to the needle distal end, when viewed along the longitudinal axis, is less than 15 degrees.

21. The instrument of claim 20, wherein a radial distance from a longitudinal axis of the spacer, to the needle distal end, is in the range from 0.7 to 1.4 inches.

22. A method of treating urinary incontinence in a male, the method comprising
creating a pair of lateral incisions substantially adjacent a patient's obturator foramen,
creating a medial incision at the perineum, medial to the pair of lateral incisions,
providing a surgical instrument comprising,
a handle having a longitudinal axis and an elongate width dimension normal to the longitudinal axis, the elongate width dimension defining a midplane,
a needle portion extending from the handle along the longitudinal axis, the needle portion comprising
a spacer portion connected to the handle,
a three-dimensional region connected to the spacer portion distal from the handle, and having structure in three dimensions, and
a needle distal end at the distal end of the three-dimensional region, the needle distal end comprising a functional section that engages a surgical implant,
providing an implantable assembly adapted for treating the incontinence, the assembly having a surface complementary to the functional section,
engaging the functional section of the needle distal end with the surface of the implantable assembly,
passing the three-dimensional region having the functional section between a lateral incision and the medial incision and through an obturator foramen by grasping the handle with the midplane approximately parallel to the palm and rotating the handle using the hand such that
during the rotation the handle rotates at least ninety degrees, and
during ninety degrees of the rotation the hand traverses ninety degrees between a forty-five degree open palm and a forty-five degree closed palm, wherein
the needle distal end is located at an angle between 20 to 70 degrees from the midplane, when viewed along the longitudinal axis, and
an angle between an axis of the needle end portion, and the midplane, the angle being an acute angle defined by the needle tip, an intersection of the axis and midplane, and the longitudinal axis, when viewed along the longitudinal axis, is in the range from 30 degrees to 60 degrees.

23. The method of claim 22, wherein the functional section of the tool is capable of dissecting tissue.

24. The method of claim 22, wherein the functional section of the tool comprises a three-dimensional region of a needle.

25. The method of claim 22, wherein the surgical instrument comprises a handle having a longitudinal axis and an elongate width dimension normal to the longitudinal axis, the elongate width dimension defining a midplane, a needle portion extending from the handle along the longitudinal axis, the needle portion comprising a spacer portion connected to the handle, a three-dimensional region connected to the spacer portion distal from the handle, and having structure in three dimensions, and a needle distal end at the distal end of the three-dimensional region, wherein the needle portion is sized and shaped to extend between an incision substantially adjacent to a patient's obturator foramen, through the obturator foramen, and to a medial incision; and wherein the needle distal end is located at an angle between 20 to 70 degrees from the midplane when viewed along the longitudinal axis, and wherein an angle between an axis of the needle end portion and the midplane, the angle being an acute angle defined by the needle tip, an intersection of the axis and midplane, and the longitudinal axis when viewed along the longitudinal axis, is in the range from 30 degrees to 60 degrees, and further comprising a needle end portion at a terminal inch of the three-dimensional region that comprises a curve.

26. The method of claim 22, wherein the surgical instrument comprises a handle comprising a longitudinal axis, needle extending from the handle, the needle comprising a spacer portion connected to the handle, and a three-dimensional region connected to the spacer portion distal from the handle, and having structure in three dimensions including a needle distal end at the distal end of the three-dimensional region, wherein the needle portion is sized and shaped to extend between an incision substantially adjacent to a patient's obturator foramen, through the obturator foramen, and to a perineal incision; the three-dimensional region has a length in the range from 2.3 to 5 inches and a diameter in the range from 2.3 to 5 inches, and an axis of the needle end portion lies within a plane that is orthogonal to the longitudinal axis of the tool, wherein an angle between an axis of the needle end portion and a tangent of a circle having an origin at the longitudinal axis and a radius extending to the needle distal end, when viewed along the longitudinal axis, is less than 15 degrees.

* * * * *

UNITED STATES PATENT AND TRADEMARK OFFICE
CERTIFICATE OF CORRECTION

| | | |
|---|---|---|
| PATENT NO. | : 7,422,557 B2 | Page 1 of 1 |
| APPLICATION NO. | : 11/347553 | |
| DATED | : September 9, 2008 | |
| INVENTOR(S) | : Kevin R. Arnal, Christian Gozzi and Peter Rehder | |

It is certified that error appears in the above-identified patent and that said Letters Patent is hereby corrected as shown below:

In column 31, line 16, and line 28, "14 centimeters" should be -- 1-4 centimeters --.

Signed and Sealed this
Twelfth Day of April, 2011

David J. Kappos
*Director of the United States Patent and Trademark Office*